(12) United States Patent
Arahira et al.

(10) Patent No.: US 10,588,503 B2
(45) Date of Patent: Mar. 17, 2020

(54) METHODS AND MEDICAL ELONGATE BODIES

(71) Applicant: TERUMO KABUSHIKI KAISHA, Shibuya-ku, Tokyo (JP)

(72) Inventors: Shouta Arahira, Shizuoka (JP); Hironori Shiga, Shizuoka (JP); Kenji Oyama, Kanagawa (JP); Yuusuke Sekine, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/470,114

(22) Filed: Mar. 27, 2017

(65) Prior Publication Data

US 2017/0281140 A1    Oct. 5, 2017

(30) Foreign Application Priority Data

Mar. 29, 2016  (JP) ................................. 2016-066899
Mar. 29, 2016  (JP) ................................. 2016-066900

(51) Int. Cl.
| | |
|---|---|
| *A61B 5/0215* | (2006.01) |
| *A61B 17/3207* | (2006.01) |
| *A61L 27/52* | (2006.01) |
| *A61M 31/00* | (2006.01) |
| *A61B 1/313* | (2006.01) |

(Continued)

(52) U.S. Cl.
CPC ............ *A61B 1/3137* (2013.01); *A61B 1/012* (2013.01); *A61B 5/02158* (2013.01);
(Continued)

(58) Field of Classification Search
CPC .................................................... A61M 31/00
See application file for complete search history.

(56) References Cited

U.S. PATENT DOCUMENTS

| | | | | |
|---|---|---|---|---|
| 4,898,575 A | * | 2/1990 | Fischell | ............. A61B 17/3207 604/22 |
| 5,370,653 A | * | 12/1994 | Cragg | ................... A61B 17/22 600/569 |

(Continued)

FOREIGN PATENT DOCUMENTS

| | | |
|---|---|---|
| JP | 2001-523142 A | 11/2001 |
| JP | 2008-541835 A | 11/2008 |

(Continued)

OTHER PUBLICATIONS

Japanese Office Action dated Aug. 27, 2019 issued in corresponding Japanese Patent Application No. 2016-066900, with English translation (6 pages).

(Continued)

*Primary Examiner* — Jacqueline Woznicki
(74) *Attorney, Agent, or Firm* — Buchanan Ingersoll & Rooney PC

(57) ABSTRACT

A method and a medical elongate body are configured to prevent stagnation or turbulence of blood flow in a recess of a rugged pattern formed in a blood vessel due to bulging of a blood vessel wall at a lesion part of the blood vessel. The method involves partitioning an inside of the blood vessel into upstream and downstream sides of the recess, and introducing gel into the recess to at least partially fill the recess. A blood vessel lumen forming method and medical elongate body to form such a lumen are other aspects of the disclosure and involve introducing gel into the recess to at least partially fill the recess with the gel, and drilling the gel to remove at least some of the gel to form a passage and secure blood flow in the blood vessel.

7 Claims, 20 Drawing Sheets

(51) Int. Cl.
*A61B 1/012* (2006.01)
*A61B 17/12* (2006.01)
*A61L 27/50* (2006.01)
*A61M 25/10* (2013.01)
*A61B 5/00* (2006.01)
*A61B 17/00* (2006.01)
*A61B 17/22* (2006.01)
*A61M 5/178* (2006.01)

(52) U.S. Cl.
CPC ...... *A61B 5/6853* (2013.01); *A61B 17/12036* (2013.01); *A61B 17/12045* (2013.01); *A61B 17/12109* (2013.01); *A61B 17/12186* (2013.01); *A61B 17/320758* (2013.01); *A61L 27/507* (2013.01); *A61L 27/52* (2013.01); *A61M 25/1011* (2013.01); *A61B 17/12181* (2013.01); *A61B 17/12195* (2013.01); *A61B 17/3207* (2013.01); *A61B 17/320725* (2013.01); *A61B 2017/00623* (2013.01); *A61B 2017/22054* (2013.01); *A61B 2017/22067* (2013.01); *A61B 2017/22081* (2013.01); *A61B 2017/22082* (2013.01); *A61B 2017/22094* (2013.01); *A61M 31/00* (2013.01); *A61M 2005/1787* (2013.01); *A61M 2025/105* (2013.01); *A61M 2025/109* (2013.01); *A61M 2025/1052* (2013.01); *A61M 2025/1081* (2013.01); *A61M 2025/1084* (2013.01); *A61M 2202/00* (2013.01); *A61M 2202/0007* (2013.01); *A61M 2202/0064* (2013.01); *A61M 2202/0078* (2013.01); *A61M 2202/04* (2013.01); *A61M 2202/0468* (2013.01); *A61M 2205/3344* (2013.01); *A61M 2210/12* (2013.01)

(56) References Cited

U.S. PATENT DOCUMENTS

| | | | | |
|---|---|---|---|---|
| 5,380,273 A * | 1/1995 | Dubrul | ............... | A61B 17/22 601/3 |
| 5,474,530 A * | 12/1995 | Passafaro | ......... | A61B 17/22012 601/2 |
| 5,725,568 A * | 3/1998 | Hastings | .......... | A61B 17/12036 606/191 |
| 5,868,708 A | 2/1999 | Hart et al. | | |
| 5,985,307 A * | 11/1999 | Hanson | ..................... | A61F 2/06 424/423 |
| 6,063,069 A * | 5/2000 | Cragg | ..................... | A61B 17/22 604/22 |
| 6,159,197 A | 12/2000 | Heuser | | |
| 6,569,129 B1 * | 5/2003 | Holmes, Jr. | ............ | A61B 17/22 604/164.06 |
| 6,635,027 B1 * | 10/2003 | Cragg | ..................... | A61B 17/22 604/22 |
| 2002/0058986 A1 * | 5/2002 | Landau | ................... | A61F 2/064 623/1.13 |
| 2005/0260157 A1 * | 11/2005 | Tremble | ............... | A61K 48/005 424/93.2 |
| 2006/0271093 A1 | 11/2006 | Holman et al. | | |
| 2006/0286141 A1 * | 12/2006 | Campbell | ................. | A61F 2/91 424/423 |
| 2007/0265563 A1 | 11/2007 | Heuser | | |
| 2011/0082534 A1 * | 4/2011 | Wallace | ............ | A61M 37/0092 623/1.11 |
| 2016/0143756 A1 * | 5/2016 | Rezac | ....................... | A61F 2/88 623/1.13 |

FOREIGN PATENT DOCUMENTS

| | | |
|---|---|---|
| JP | 2011-509158 A | 3/2011 |
| JP | 2013-198668 A | 10/2013 |
| WO | 96/18427 A1 | 6/1996 |
| WO | WO 2009/089343 A1 | 7/2009 |
| WO | 2015074302 A1 | 5/2015 |

OTHER PUBLICATIONS

Office Action (Notice of Reasons for Refusal) dated Nov. 5, 2019, by the Japanese Patent Office in corresponding Japanese Patent Application No. 2016-066899 and an English Translation of the Office Action. (8 pages).

* cited by examiner

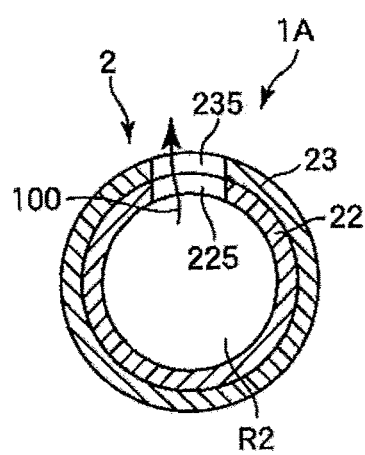 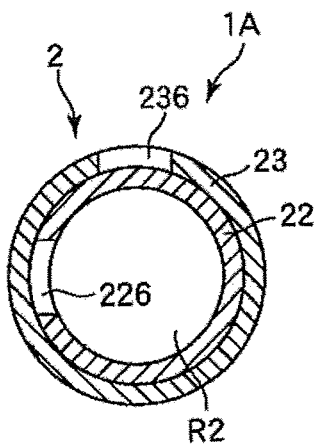 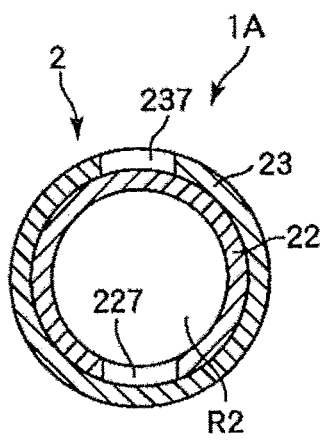
FIG.6A　　　FIG.6B　　　FIG.6C
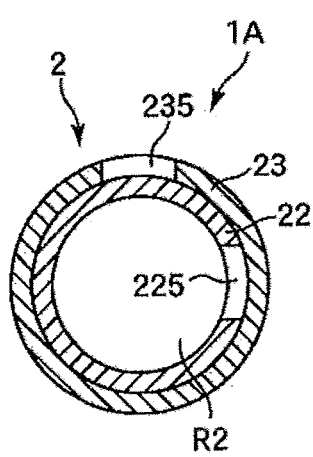 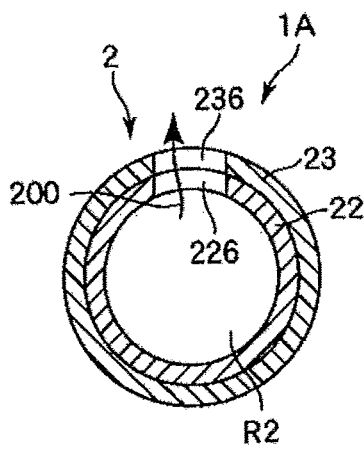 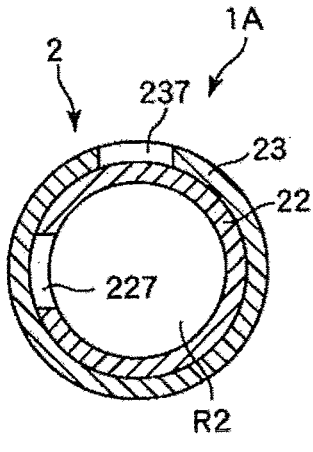
FIG.7A　　　FIG.7B　　　FIG.7C
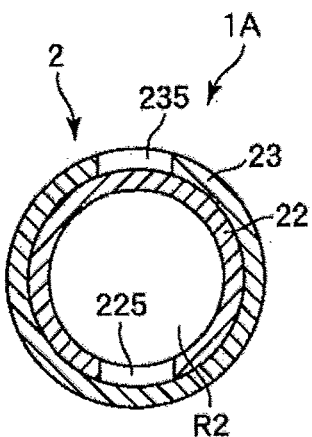 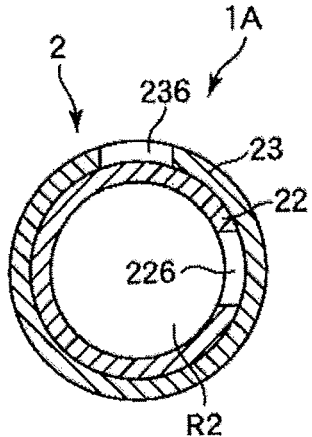 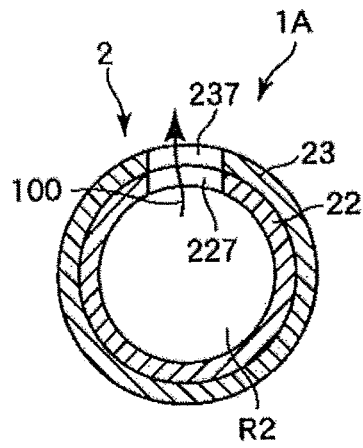
FIG.8A　　　FIG.8B　　　FIG.8C

METHODS AND MEDICAL ELONGATE BODIES

This application claims priority to Japanese Application No. 2016-066899 filed on Mar. 29, 2016 and Japanese Application No. 2016-066900 filed on Mar. 29, 2016, the entire content of both of which is incorporated herein by reference.

TECHNICAL FIELD

The present disclosure generally relates to methods and medical elongate bodies for filling recesses in a blood vessel wall at a lesion site in a blood vessel and for forming a blood vessel lumen at a lesion site in a blood vessel.

BACKGROUND DISCUSSION

A rugged pattern (projections and recesses) may exist interiorly in a blood vessel at a blood vessel wall due to bulging of the blood vessel wall to the inside of the blood vessel, the bulging arising, for example, from a thrombus formed at the blood vessel wall, arterial sclerosis, plaque which is a macular hypertrophic lesion of an inner membrane present at a focus of arterial sclerosis, medial type calcification, etc. Depending on the extent of the ruggedness, stagnation or turbulence of blood flow may occur in hollows (recesses) of the rugged pattern, possibly leading to thrombus formation. As means for smoothening such a rugged pattern, there has been known a treatment using a catheter as disclosed in Japanese Application Publication No. 2011-509158.

The catheter described in Japanese Application Publication No. 2011-509158 is a medical device for treatment of plaque, and includes a catheter body and a freely inflatable and deflatable balloon assembly provided at a distal portion of the catheter body. In addition, the balloon assembly has a jet section for jetting a plaque removing agent. By use of this catheter, the following treatment is conducted.

First, the catheter is pushed forward in a blood vessel until the balloon assembly is located at a plaque. Next, the balloon assembly is inflated, and the plaque removing agent is jetted out from the jet section, to remove the plaque. Then, a stent is placed indwelling at that part of the blood vessel where the plaque has been removed. By this, the plaque is removed, and a sufficient inside diameter of the blood vessel can be secured.

Depending on the kind and extent of the rugged pattern formed in the blood vessel, however, it may be difficult to treat the rugged pattern by a treatment method in which the catheter as above-described is used. For example, in the above-mentioned treatment method, rugged patterns arising from a thrombus with diverse features such as size and shape of the rugged pattern generated at a blood vessel wall or arising from medial type calcification cannot be smoothened. Further, in a case where the extent of projections and recesses in the rugged pattern due to plaque is large, it may be impossible to insert the catheter and, therefore, it may be impossible to perform the intended treatment.

SUMMARY

The method and medical elongate body disclosed here are able to inhibit or prevent stagnation or turbulence of blood flow in recesses of a rugged (projected and recessed) pattern formed in a blood vessel due to bulging of a blood vessel wall at a lesion part of the blood vessel, regardless of the kind or extent of the hollows.

According to one aspect, a method for filling, with a gel, a recess located in a blood vessel wall at a lesion site in a blood vessel comprises: partitioning an inside of the blood vessel into an upstream side located upstream of the recess and a downstream side located downstream of the recess; and introducing the gel into the recess when the inside of the blood vessel is partitioned to at least partially fill-up the recess with the gel.

A medical elongate body may be used in the filling, the medical elongate body provided with a jet port portion formed with a jet port for jetting the gel and which is inflatable and deflatable.

The jet balloon section may be configured to jet the gel in an inflated state, and, during the introduction of the gel, the jet balloon section may be inflated while restricting a limit of inflation of the jet port portion and the gel may be jetted.

During the introduction of the gel, an outer circumference portion of the jet port formed portion in a longitudinal sectional shape of the medical elongate body may be restricted in such a manner as to be rectilinear along a longitudinal direction of the medical elongate body.

The jet balloon section may be configured to be inflated by supply of a working fluid, and, in the filling, the gel may be supplied to the jet balloon section as the working fluid.

In the filling method as above, the medical elongate body may include a distal-side balloon section which is provided on a distal side of the jet port formed portion and is inflatable and deflatable, and a proximal-side balloon section which is provided on a proximal side of the jet port formed portion and is inflatable and deflatable, and, the distal-side balloon section and the proximal-side balloon section may be inflated to partition the inside of the blood vessel.

During the partitioning, the distal-side balloon section may be inflated prior to the proximal-side balloon section.

When the medical elongate body is inserted into the blood vessel, the medical elongate body may be inserted from a downstream side toward an upstream side with respect to the blood vessel.

Another aspect disclosed here involves a method for smoothening a rugged blood vessel inner wall surface at a lesion site of the blood vessel, wherein the rugged blood vessel inner wall surface includes a plurality of spaced-apart recesses in the blood vessel. The method comprises: moving a catheter in the blood vessel to position a distal portion of the catheter adjacent the rugged blood vessel inner wall surface at the lesion site; ejecting gel from the distal portion of the catheter while the distal portion of the catheter is positioned adjacent the rugged blood vessel inner wall surface to deliver the gel into the blood vessel; and filling at least one of the recesses with the gel.

Another aspect involves a medical elongate body including: an elongate catheter body possessing a distal end and configured to be inserted into a blood vessel starting from the distal end; an inflatable and deflatable balloon at a distal portion of the catheter body; a restricting section provided at the balloon to restrict a limit of inflation of the balloon; with the balloon including a jet port portion that includes a jet port for jetting gel into a blood vessel while the balloon is positioned in the blood vessel, and with the restricting section being located to restrict the limit of inflation of at least the jet port portion.

The restricting section may be configured to be expandable and contractible.

The restricting section may be provided on an outer circumference side of the jet port formed portion.

The restricting section may be composed of a net-like body.

According to the present disclosure, recesses or hollows generated in a blood vessel wall are filled up with a gel, whereby stagnation or turbulence of blood flow in the recesses or hollows can be prevented from occurring. As a result, the blood flow in the vicinity of the recesses or hollows can be normalized. Therefore, formation of a thrombus, which would plug up the blood vessel or hinder blood flow, in a rugged (projected and recessed) pattern generated in the blood vessel wall can be prevented. Particularly, the rugged pattern can be easily smoothened, regardless of the extent or kind of the rugged pattern, in other words, no matter which of a thrombus, a plaque, medial type calcification and the like may be the cause of the rugged pattern.

According to the present disclosure, by filling with a gel a hollow or hollows (recess or recesses) of a rugged pattern generated in a blood vessel wall and drilling the gel made to fill up the recesses or hollows to thereby removing, a blood passage having a smooth inner circumferential surface can be formed, regardless of the extent of the ruggedness. Therefore, blood flow in the vicinity of the recesses or hollows of the rugged pattern generated at the blood vessel wall can be normalized and smoothened.

Particularly, according to the present disclosure, recesses or hollows of rugged patterns with various sizes, shapes, etc. are securely filled up with the gel. Therefore, stagnation or turbulence of blood in the vicinity of the hollows can be prevented from occurring. As a result, even if a rugged pattern is generated in a blood vessel wall, formation of a thrombus which would occlude a blood vessel or hamper blood flow can be prevented from occurring.

According to another aspect, a blood vessel lumen forming method comprises: introducing gel into a recess of a rugged pattern in a blood vessel wall at a lesion site in a blood vessel to at least partially fill the recess with the gel, and drilling the gel to remove at least some of the gel to form a passage and secure blood flow.

Another aspect involves a medical elongated body comprising: a flexible elongated body possessing a distal end and configured to be inserted into a blood vessel starting from the distal end; a jet section configured to jet gel into the blood vessel while the elongated body is positioned in the blood vessel; and a drilling unit at a distal end portion of the elongated body and configured to drill the gel jetted by the jet section in the blood vessel.

BRIEF DESCRIPTION OF THE DRAWINGS

FIGS. 2A to 2C are cross-sectional views showing the inside of a blood vessel formed with hollows or recesses, for explaining a first embodiment of a filling method according to the present disclosure, wherein FIG. 2A illustrates a state in which the medical elongate body has not yet been inserted in the blood vessel, FIG. 2B illustrates a state in which the medical elongate body is inserted along a guide wire, and FIG. 2C illustrates a state in which a distal-side balloon section is inflated;

FIGS. 3A to 3C are cross-sectional views showing the inside of a blood vessel formed with hollows or recesses, for explaining the first embodiment of the filling method according to the present disclosure, wherein FIG. 3A illustrates a state in which a jet balloon and a proximal-side balloon section are exposed, FIG. 3B illustrates a state in which the proximal-side balloon section is inflated, and FIG. 3C illustrates a state in which the hollows or recesses are filled up with a gel;

FIGS. 4A to 4C are cross-sectional views showing the inside of a blood vessel formed with hollows, for explaining the first embodiment of the filling method according to the present disclosure, wherein FIG. 4A illustrates a state in which a balloon unit is deflated, FIG. 4B illustrates a state in which the medical elongate body is retracted into an outer tube, and FIG. 4C illustrates a state in which the medical elongate body is withdrawn out of the blood vessel;

FIGS. 6A to 6C illustrate a state in which a distal-side balloon of the medical elongate body shown in FIG. 5 is being inflated, wherein FIG. 6A is a cross-sectional view taken along the section line A-A of FIG. 5, FIG. 6B is a cross-sectional view taken along the section line B-B of FIG. 5, and FIG. 6C is a cross-sectional view taken along the section line C-C of FIG. 5;

FIGS. 7A to 7C illustrate a state in which a jet balloon section of the medical elongate body shown in FIG. 5 is being inflated, wherein FIG. 7A is a cross-sectional view taken along the section line A-A of FIG. 5, FIG. 7B is a cross-sectional view taken along the section line B-B of FIG. 5, and FIG. 7C is a cross-sectional view taken along the section line C-C of FIG. 5;

FIGS. 8A to 8C illustrate a state in which a proximal-side balloon section of the medical elongate body shown in FIG. 5 is being inflated, wherein FIG. 8A is a cross-sectional view taken along the section line A-A of FIG. 5, FIG. 8B is a cross-sectional view taken along the section line B-B of FIG. 5, and FIG. 8C is a cross-sectional view taken along the section line C-C of FIG. 5;

FIGS. 10A to 10C are enlarged longitudinal cross-sectional views of a distal portion of a catheter body of the medical elongate body shown in FIG. 9, wherein FIG. 10A illustrates a first communication state, FIG. 10B illustrates a second communication state, and FIG. 10C illustrates a third communication state;

FIGS. 14A to 14C are cross-sectional views illustrating the inside of a blood vessel formed with a rugged, projected and recessed pattern, for explaining a sixth embodiment of the blood vessel lumen forming method according to the present disclosure, wherein FIG. 14A illustrates a state before the medical elongated body is inserted into the blood vessel, FIG. 14B illustrates a state in which the medical elongated body is inserted in the blood vessel, and FIG. 14C illustrates a state in which a balloon unit is expanded;

FIGS. 15A to 14C are cross-sectional views illustrating the inside of the blood vessel formed with the rugged pattern, for explaining the sixth embodiment of the blood vessel lumen forming method according to the present disclosure, wherein FIG. 15A illustrates a state in which a gel is jetted from a jet section.

FIGS. 16A to 16C are cross-sectional views illustrating the inside of the blood vessel formed with the rugged pattern, for explaining the sixth embodiment of the blood vessel lumen forming method according to the present disclosure, wherein FIG. 16A illustrates a state in which the gel is being drilled, FIG. 16B illustrates a state in which the drilling of the gel has been completed, and FIG. 16C illustrates a state in which the medical elongated body has been withdrawn out of the blood vessel;

FIGS. 17A to 17C are cross-sectional views illustrating the inside of a blood vessel formed with a rugged pattern, for explaining a seventh embodiment of the blood vessel lumen forming method according to the present disclosure, wherein FIG. 17A illustrates a state in which filling with a gel has been completed and a balloon unit is contracted, FIG. 17B illustrates a state in which the gel is being drilled together with crests of the rugged pattern, and FIG. 17C illustrates a state in which the medical elongated body has been withdrawn out of the blood vessel;

FIGS. 20A to 20C are cross-sectional views illustrating the inside of a blood vessel formed with a rugged pattern, for explaining the eighth embodiment of the blood vessel lumen forming method according to the present disclosure, wherein FIG. 20A illustrates a state in which blood pressure is being detected, FIG. 20B illustrates a state in which drilling is under way, and FIG. 20C illustrates a state in which the drilling has been completed;

FIGS. 22A to 22C are cross-sectional views illustrating the inside of a blood vessel formed with a rugged pattern, for explaining the ninth embodiment of the blood vessel lumen forming method according to the present disclosure, wherein FIG. 22A illustrates a state in which the medical elongated body is inserted in the blood vessel, FIG. 22B illustrates a state in which a balloon unit is expanded, and FIG. 22C illustrates a state in which hollows are filled up with a gel; and FIGS. 23A to 23C are cross-sectional views illustrating the inside of the blood vessel formed with the rugged pattern, for explaining the ninth embodiment of the blood vessel lumen forming method according to the present disclosure, wherein FIG. 23A illustrates a state in which the medical elongated body has temporarily been retracted to a proximal side, FIG. 23B illustrates a state in which drilling is under way, and FIG. 23C illustrates a state in which the drilling has been completed.

DETAILED DESCRIPTION

The filling method and the medical elongate body according to the described aspects of the present disclosure will be described in detail below, with reference to preferred embodiments illustrated in the accompanying drawings and representing examples of the inventive filling method and medical elongate body disclosed here.

<First Embodiment>

Figure 1:
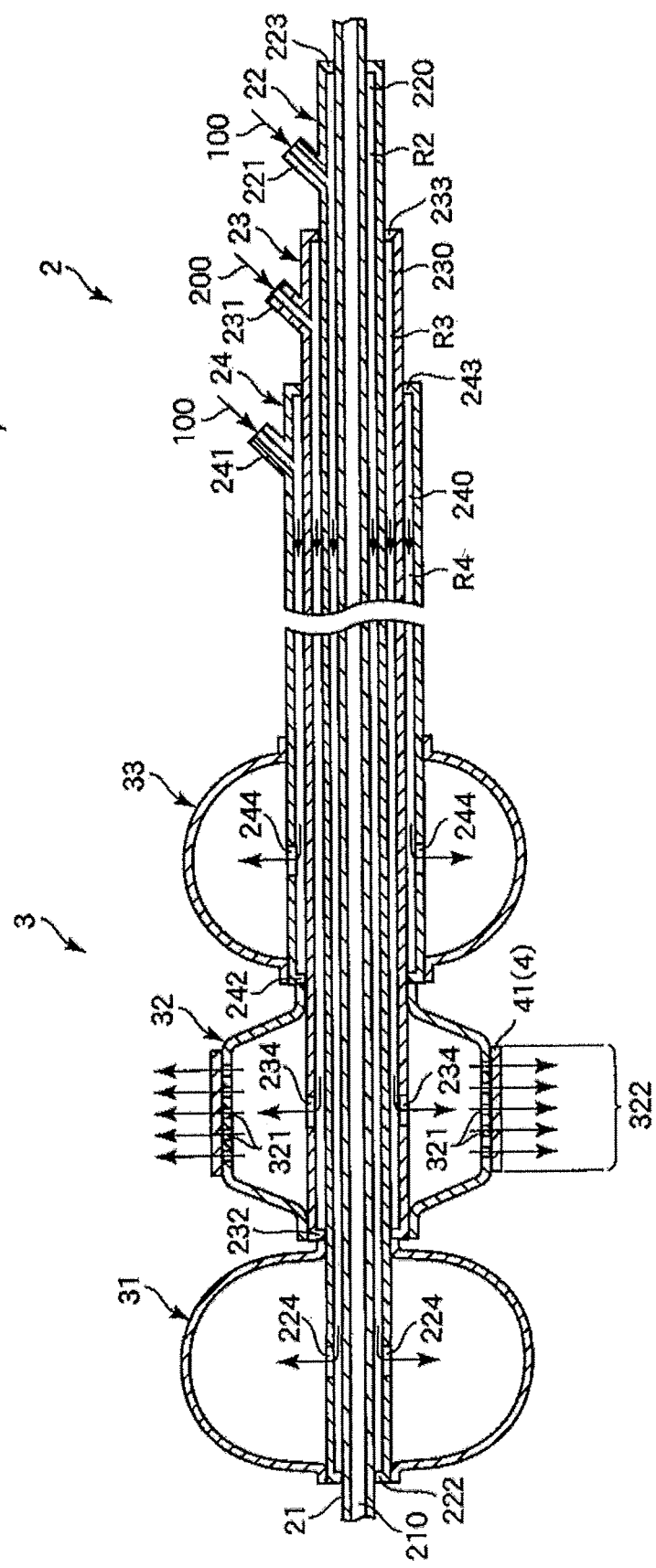
FIG. 1 is a longitudinal cross-sectional view showing a first embodiment of a medical elongate body according to the present disclosure.
Figure 2A:
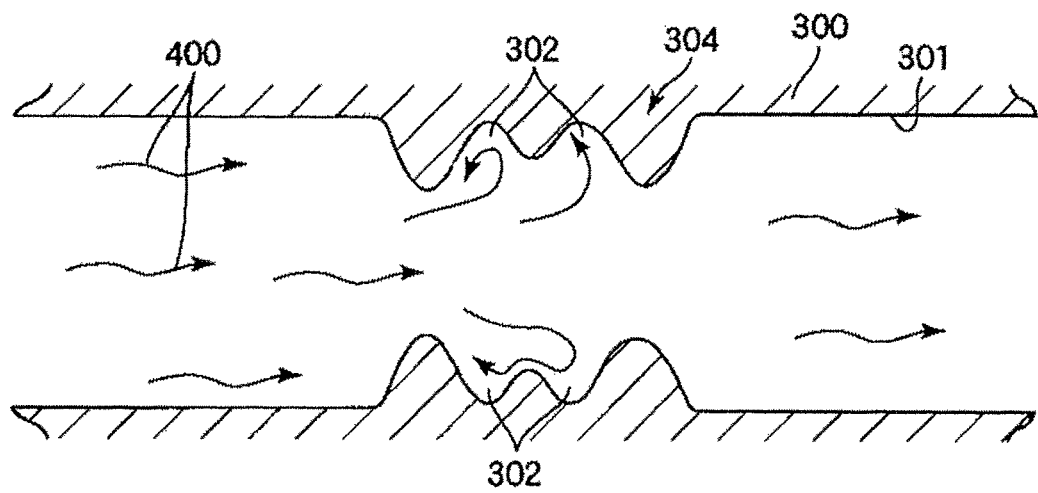
Figure 2B:
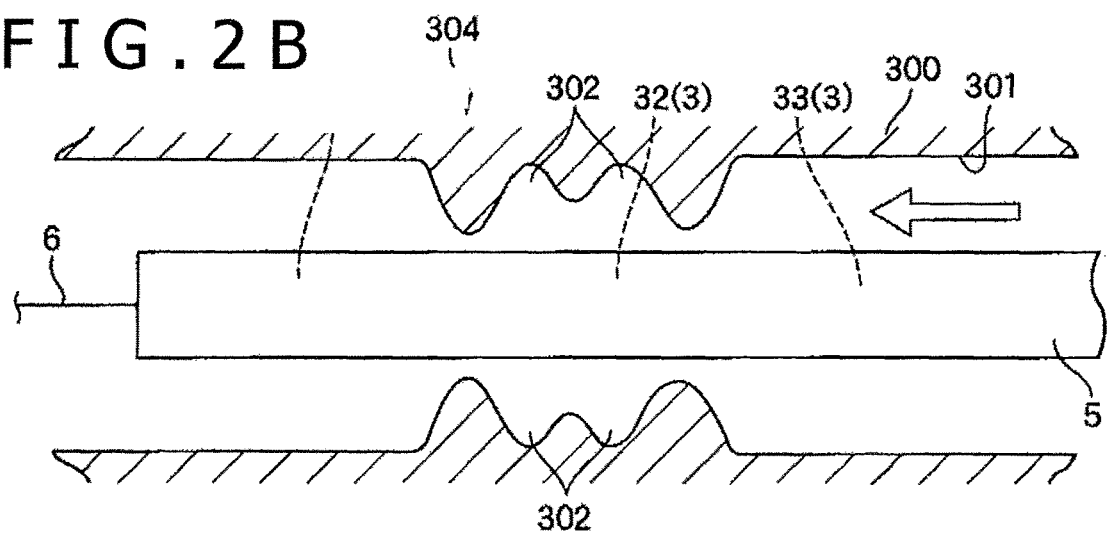
Figure 2C:
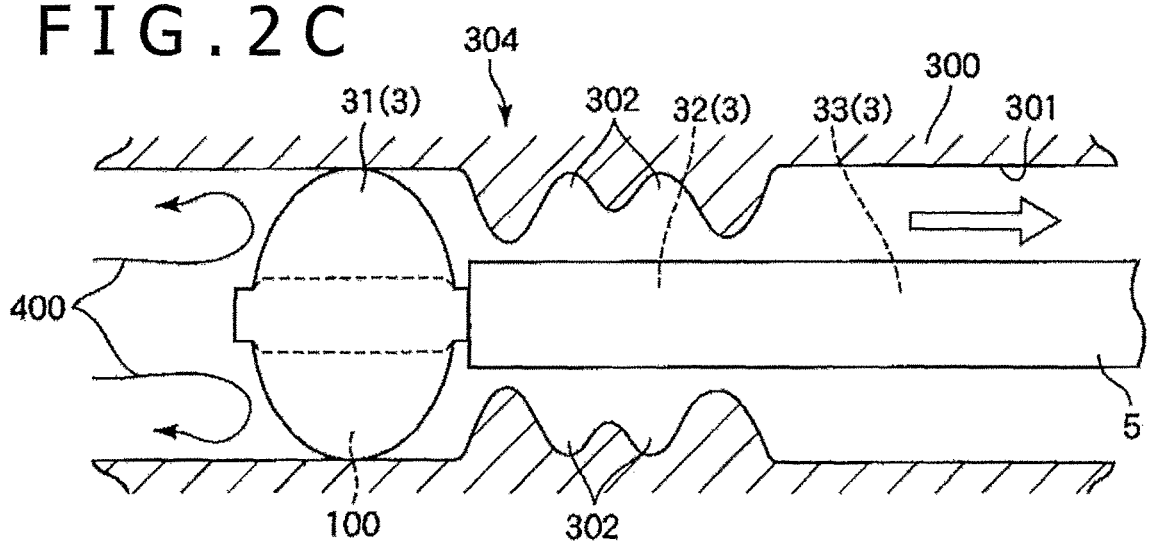
Figure 3A:
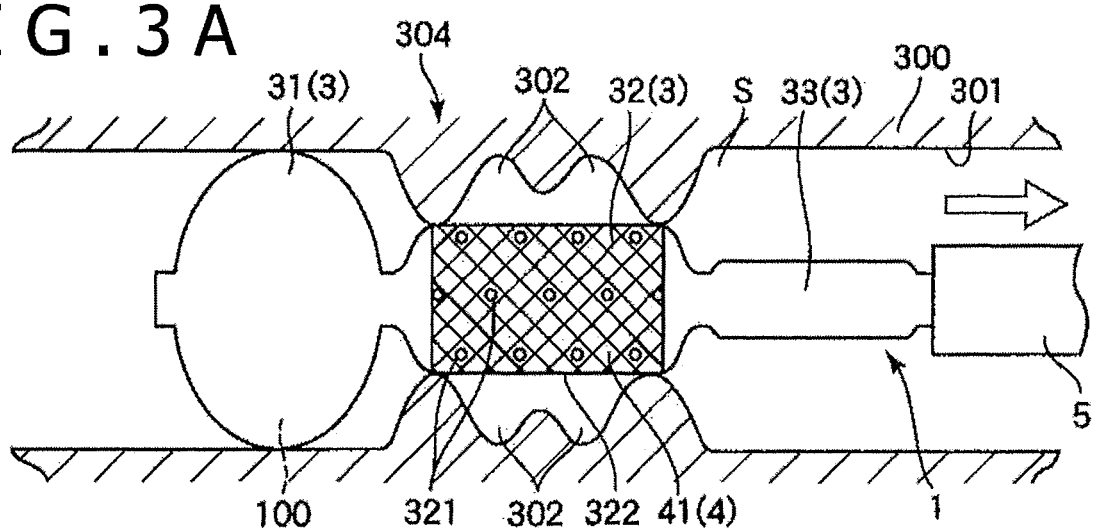
Figure 3B:
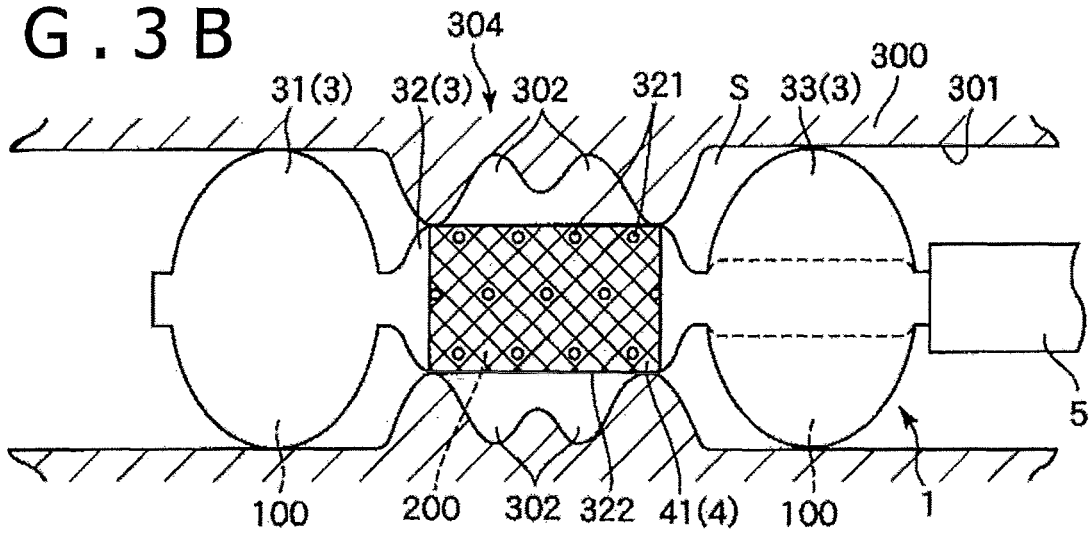
Figure 3C:
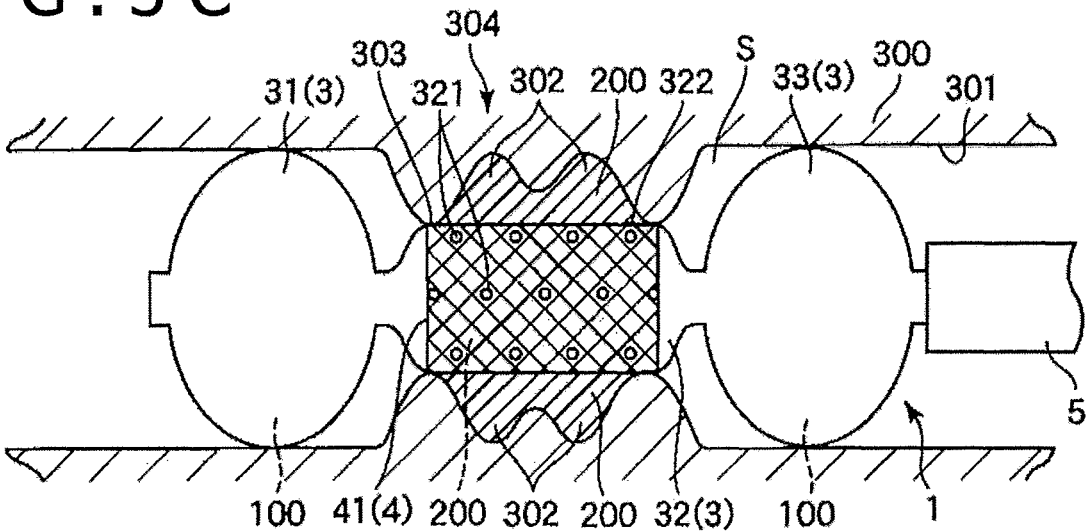
Figure 4A:
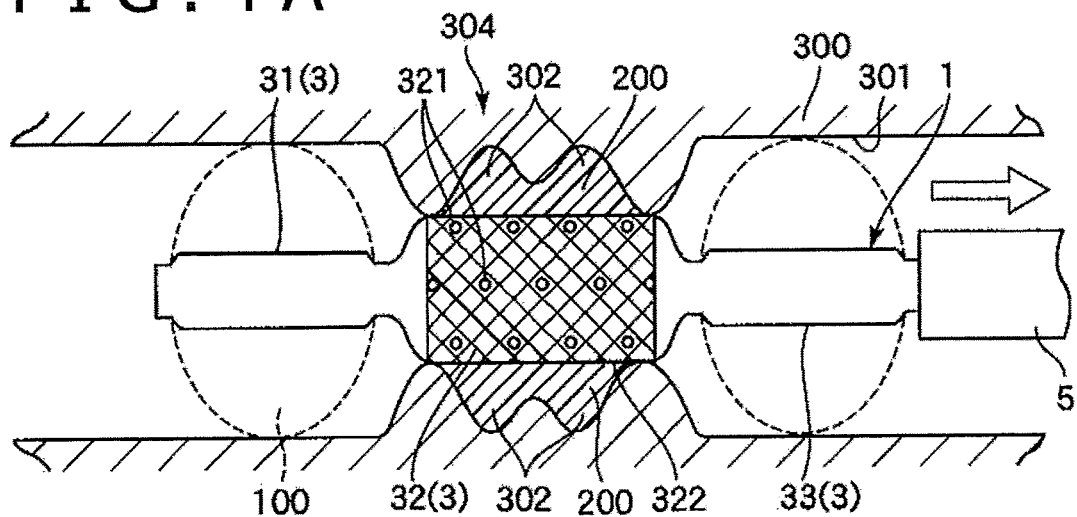
Figure 4B:
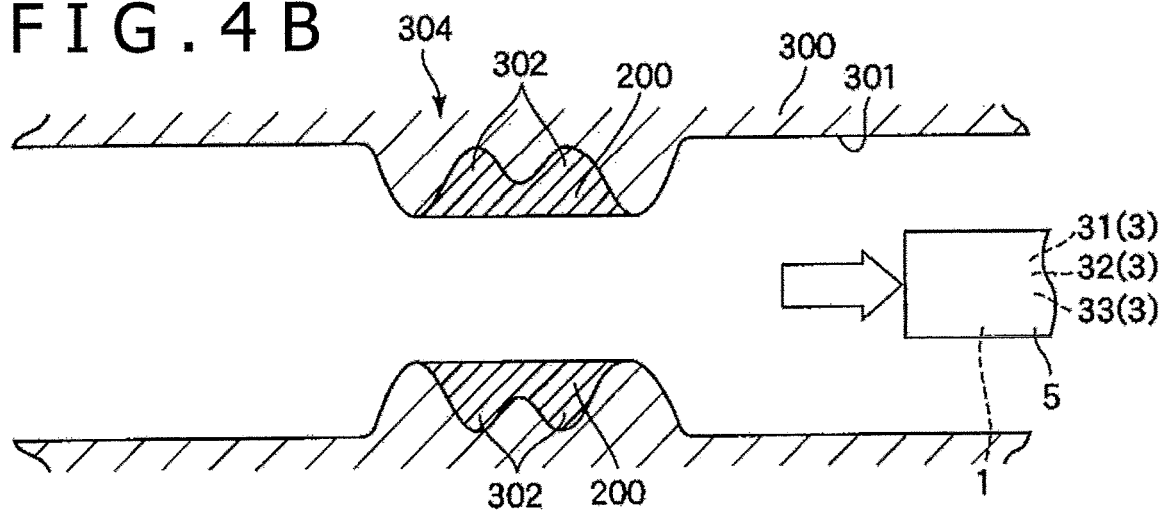
Figure 4C:
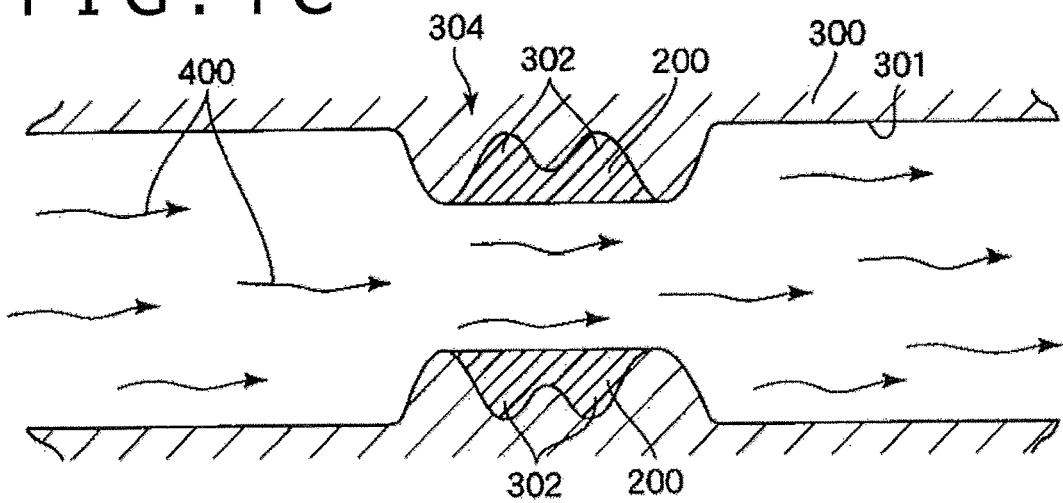

FIG. 1 is a longitudinal cross-sectional view showing a first embodiment of a medical elongate body according to the present disclosure. FIGS. 2A to 2C are cross-sectional views showing the inside of a blood vessel formed with hollows or recesses, for explaining a first embodiment of a filling method according to the present disclosure, wherein FIG. 2A illustrates a state in which the medical elongate body has not yet been inserted in the blood vessel, FIG. 2B illustrates a state in which the medical elongate body is inserted along a guide wire, and FIG. 2C illustrates a state in which a distal-side balloon section is inflated. FIGS. 3A to 3C are cross-sectional views showing the inside of a blood vessel formed with hollows, for explaining the first embodiment of the filling method according to the present disclosure, wherein FIG. 3A illustrates a state in which a jet balloon and a proximal-side balloon section are exposed, FIG. 3B illustrates a state in which the proximal-side balloon section is inflated, and FIG. 3C illustrates a state in which the hollows or recesses are filled with a gel. FIGS. 4A to 4C are cross-sectional views showing the inside of a blood vessel formed with hollows or recesses, for explaining the first embodiment of the filling method according to the present disclosure, wherein FIG. 4A illustrates a state in which a balloon unit is deflated, FIG. 4B illustrates a state in which the medical elongate body is retracted into an outer tube, and FIG. 4C illustrates a state in which the medical elongate body is drawn out of the blood vessel.

In the description which follows, for convenience of description, the right side in FIGS. 1 to 4C (and also in FIGS. 5 to 12) will be referred to as "proximal end," and the left side as "distal end." In addition, for easy understanding, in FIGS. 1 to 4C (and also in FIGS. 5 to 12), the dimensions in the longitudinal direction of the medical elongate body are scaled down, while the dimensions in the radial direction are scaled up. Therefore, the dimensions of the medical elongate body, particularly of balloons, in the drawings may be quite different from the actual dimensions.

As illustrated in FIG. 1, a medical elongate body 1 includes an elongate catheter body 2, a balloon unit 3 provided at a distal portion of the catheter body 2, and a restricting section 4.

The catheter body 2 has a quadruple tube structure including a first catheter 21, a second catheter 22, a third catheter 23, and a fourth catheter 24. The first catheter 21, the second catheter 22, the third catheter 23 and the fourth catheter 24 are arranged concentrically in this order from inside to the outside.

As shown in FIG. 1, the first catheter 21 has a lumen 210 in the inside of the first catheter 21. In the lumen 210, there is inserted and passed, for example, a guide wire or the like. The length of the first catheter 21, in this embodiment, is greater than the length of the second catheter 22, is greater than the length of the third catheter 23 and is greater than the length of the fourth catheter 24. A distal portion of the first catheter 21 is exposed from a distal end of the second catheter 22, and a proximal portion of the first catheter 21 is exposed from a proximal end of the second catheter 22.

The second catheter 22 has a lumen 220. In the lumen 220 is inserted the first catheter 21. In addition, an inner circumference portion of the second catheter 22 is spaced apart from an outer circumference portion of the first catheter 21. Therefore, a space is defined between the inner circumference portion of the second catheter 22 and the outer circumference portion of the first catheter 21, and this space functions as a passage R2.

In addition, the proximal portion of the second catheter 22 is provided with a side port 221, specifically, that portion of the second catheter 22 which is exposed from a proximal portion of the third catheter 23. The side port 221 communicates with the passage R2. This structure permits a fluid to be supplied into the passage R2 via the side port 221.

The distal inner circumference portion of the second catheter 22 is provided with a flange 222, which projects to the inside in a flange shape and by which the space between the second catheter 22 and the first catheter 21 is stopped up (blocked). By this structure, a fluid in the passage R2 is prevented from flowing out from a distal portion of the second catheter 22. In addition, the proximal inner circumference portion of the second catheter 22 is provided with a flange 223, which is formed to project to the inside in a flange shape and by which the space between the second catheter 22 and the first catheter 21 is stopped up (blocked). By this structure, the fluid in the passage R2 is prevented from flowing out from a proximal portion of the second catheter 22.

The second catheter 22 is provided in the vicinity of a distal portion of the second catheter 22 with through-holes 224 which penetrate a tube wall of the second catheter 22 in the thickness direction of the tube wall. In this embodiment, two such through-holes 224 are provided. These through-holes 224 function as supply ports for supplying the fluid in the passage R2 into a distal-side balloon 31 which will be described later.

The third catheter 23 has a lumen 230. In the lumen 230 is inserted the second catheter 22. In addition, an inner circumference portion of the third catheter 23 is spaced apart from an outer circumference portion of the second catheter 22. Therefore, a space is defined between the inner circumference portion of the third catheter 23 and the outer circumference portion of the second catheter 22, and this space functions as a passage R3.

In addition, a proximal portion of the third catheter 23 is provided with a side port 231, specifically that portion of the third catheter 23 which is exposed from a proximal portion of the fourth catheter 24. The side port 231 communicates with the passage R3. This structure permits a fluid to be supplied into the passage R3 via the side port 231.

A distal inner circumferential portion of the third catheter 23 is provided with a flange 232, which projects to the inside in a flange shape and by which the space between the third catheter 23 and the second catheter 22 is stopped up (blocked). By this structure, a fluid in the passage R3 is prevented from flowing out from a distal portion of the third catheter 23. In addition, a proximal inner circumferential portion of the third catheter 23 is provided with a flange 233, which projects to the inside in a flange shape and by which the space between the third catheter 23 and the second catheter 22 is stopped up (blocked). By this structure, the fluid in the passage R3 is prevented from flowing out from a proximal portion of the third catheter 23.

A distal portion of the third catheter 23 is provided with through-holes 234 which penetrate a tube wall of the third catheter 23 in the thickness direction of the tube wall. In this embodiment, two such through-holes 234 are provided. These through-holes 234 function as supply ports for supplying the fluid in the passage R3 into a jet balloon 32 which will be described later.

The fourth catheter 24 has a lumen 240. In the lumen 240 is inserted the third catheter 23. In addition, an inner circumference portion of the fourth catheter 24 is spaced apart from an outer circumference portion of the third catheter 23. Therefore, a space is defined between the inner circumference portion of the fourth catheter 24 and the outer circumference portion of the third catheter 23, and this space functions as a passage R4.

In addition, a proximal portion of the fourth catheter 24 is provided with a side port 241, specifically that portion of the fourth catheter 24 which is located distally of the side port 231 of the third catheter 23. The side port 241 communicates with the passage R4. This structure permits a fluid to be supplied into the passage R4 via the side port 241.

A distal inner circumferential portion of the fourth catheter 24 is provided with a flange 242, which projects to the inside in a flange shape and by which the space between the fourth catheter 24 and the third catheter 23 is stopped up. This structure prevents the fluid in the passage R4 from flowing out from a distal portion of the fourth catheter 24. In addition, a proximal inner circumferential portion of the fourth catheter 24 is provided with a flange 243, which projects to the inside in a flange shape and by which the space between the fourth catheter 24 and the third catheter 23 is stopped up. By this structure, the fluid in the passage R4 is prevented from flowing out from a proximal portion of the fourth catheter 24.

The fourth catheter 24 is provided in the vicinity of a distal portion of the fourth catheter 24 with through-holes 244 which penetrate a tube wall of the fourth catheter 24 in the thickness direction of the tube wall. In this embodiment, two such through-holes 244 are provided. These through-holes 244 function as supply ports for supplying the fluid in the passage R4 into a proximal-side balloon 33 which will be described later.

Examples of the material or materials constituting the first catheter 21, the second catheter 22, the third catheter 23 and the fourth catheter 24 as above include various thermoplastic resins and thermosetting resins, such as polyolefin resins, polyamide resins, urethane resins, and polyimide resins. Specific examples include polyolefins such as polyethylene, polypropylene, ethylene-propylene copolymers or ethylene-vinyl acetate copolymers, polyvinyl chloride, polyesters such as polyethylene terephthalate or polybutylene terephthalate, polyurethane, polyamides, polyimides, polystyrene resins, fluororesins, and various thermoplastic elastomers based on styrene, polyolefin, polyvinyl chloride, polyurethane, polyester, polyamide, polybutadiene, fluororubber or the like. The first catheter 21, the second catheter 22, the third catheter 23 and the fourth catheter 24 may each have a multilayer laminate structure formed from a plurality of materials.

The first catheter 21, the second catheter 22, the third catheter 23 and the fourth catheter 24 may be configured to be movable in the longitudinal direction relative to one another and may be rotatable relative to one another.

Now, the balloon unit 3 will be described below.

As illustrated in FIG. 1, the balloon unit 3 includes the distal-side balloon 31 as a distal-side balloon section, the jet balloon 32 as a jet balloon section, and the proximal-side balloon 33 as a proximal-side balloon section. The distal-side balloon 31, the jet balloon 32 and the proximal-side balloon 33 are aligned or positioned in this order from the distal side.

The distal-side balloon 31 is provided at a distal outer circumference portion of the second catheter 22. Specifically, the distal-side balloon 31 is provided at that portion of the second catheter 22 which is exposed from (extends distally beyond) a distal end of the third catheter 23.

The distal-side balloon 31 is composed of a flexible film member. Both end portions of the distal-side balloon 31 are joined to a distal portion of the second catheter 22 by, for example, heat fusing or the like.

The distal-side balloon 31 is inflated by supplying a working fluid into distal-side balloon 31 from the side port 221 through the passage R2 and the through-holes 224. Then, the distal-side balloon 31 is deflated from the inflated state by drawing out the working fluid from the interior of the distal-side balloon 31.

In this embodiment, the working fluid supplied into the distal-side balloon 31 is a contrast medium 100. The position of the distal-side balloon 31 in a blood vessel can thus be grasped under radioscopy.

The jet balloon 32 (extension member or expansion member) is provided at the distal portion of the catheter. In this embodiment, the jet balloon 32 is provided at a distal outer circumference portion of the third catheter 23. Specifically, the jet balloon 32 is provided at that portion of the third catheter 23 which is exposed from a distal end of the fourth catheter 24.

The jet balloon 32 is composed of a flexible film member. Both end portions of the jet balloon 32 are joined to a distal portion of the third catheter 23 by, for example, heat fusing or the like.

The jet balloon 32 is inflated by supplying a working fluid into the jet balloon 32 from the side port 231 via the passage R3 and the through-holes 234. Then, the jet balloon 32 is deflated from the inflated state by drawing out the working fluid therefrom.

In addition, the jet balloon 32 is provided with a plurality of jet ports 321 constituted of through-holes that penetrate the jet balloon 32 in the film thickness direction. This structure permits the working fluid inside the jet balloon 32 to be jetted out through the jet ports 321.

In this embodiment, the working fluid supplied into the jet balloon 32 is a gel 200. This ensures that the gel 200 can be jetted out through the jet ports 321, whereby a treatment as described later can be performed.

The region of the jet balloon 32 where the jet ports 321 are formed, as depicted in FIG. 1, will be referred to as a jet port formed portion 322 (jet port portion).

The gel 200 is preferably constituted of a bio-compatible material. Examples of the applicable bio-compatible material include polyurethane, polyethylene glycol, 2-methacryloyloxyethyl phosphorylcholine (MPC) polymers having a phospholipid polar group, collagen, agarose, hyaluronic acid, chitin, chitosan, acrylic polymers, epoxy polymers, and methacrylic polymers and copolymers, such as poly(2-hydroxy methacrylate).

The gel 200 may also be admixed with a drug such as an antithrombogenic agent.

The viscosity of the gel 200 is preferably not less than 1 Pa·s and not more than 150 Pa·s. This helps ensure that after hollows or recesses 302 are filled with the gel 200, the gel 200 can be prevented from being washed away by blood, as will be described later (see FIG. 4C).

The proximal-side balloon 33 is provided at a distal outer circumference portion of the fourth catheter 24. The proximal-side balloon 33 is composed of a flexible film member. Both end portions of the proximal-side balloon 33 are joined to a distal portion of the fourth catheter 24 by, for example, heat fusing or the like.

The proximal-side balloon 33 is inflated by supplying a working fluid into the proximal-side balloon 33 from the side port 241 through the passage R4 and the through-holes 244. Then, the proximal-side balloon 33 is deflated from the inflated state by drawing out the working fluid therefrom.

In this embodiment, the working fluid supplied into the proximal-side balloon 33 is a contrast medium 100. The position of the proximal-side balloon 33 in a blood vessel can thus be grasped under radioscopy.

The materials constituting the distal-side balloon 31, the jet balloon 32 and the proximal-side balloon 33 as above may be the same or different. The constituent materials are not particularly limited. Examples of the constituent materials include polyester resins or polyester elastomers such as polyethylene terephthalate or polybutylene terephthalate, olefin resins such as polyethylene or polypropylene, which may or may not be cross-linked by irradiation with electron rays, polyvinyl chloride, polyamide resins or polyamide elastomers such as nylon 11, nylon 12, or nylon 610, polyurethane resins, ethylene-vinyl acetate copolymer which may or may not be cross-linked by irradiation with electron rays, or polymer blends, polymer alloys and the like containing at least one of these resins.

As illustrated in FIG. 1, a net-like body 41 as the restricting section 4 is provided at an outer circumference portion of the jet balloon 32. In this embodiment, the net-like body 41 is provided in such a manner as to cover the jet port formed portion 322. In this embodiment, the net-like body 41 is fixed to the outer circumference portion of the jet balloon 32.

The net-like body 41 is hollow cylindrical in general shape. The net-like (net) body 41 may be a braided body in which linear (filamentous) material is knitted or braided, a connected body in which ring-like linear materials are arrayed concentrically in one direction and connected, a spirally wound body of linear material, or a combination of them. Herein, these forms are generically referred to as the "net-like body." Such a configuration ensures that the net-like body 41 can be prevented from closing each jet port 321. In other words, openings of the net-like body 41 function as communication holes that communicate with the jet ports 321. Therefore, the gel 200 can be jetted out through the jet ports 321.

The net-like body 41 is configured to be expandable and contractible in the radial direction. In addition, the net-like body 41 has a self-expanding property, and expands from its contracted state when restriction thereon is released. In the expanded state, the net-like body 41 is hollow cylindrical in shape.

Referring to FIGS. 2A to 4C, a method of using the medical elongate body configured as above, or the filling method according to the present disclosure will be described below.

The filling method according to the present disclosure includes [1] an insertion step, [2] a partitioning step, [3] a filling step, and [4] a withdrawing step.

In the first place, a blood vessel 300 into which the medical elongate body 1 is to be inserted will be described.

As illustrated in FIG. 2A, a blood vessel wall 301 of the blood vessel 300 exhibits a rugged (projected and recessed) pattern 304 (i.e., the blood vessel possesses a rugged blood vessel inner wall surface). The rugged pattern 304 is formed by virtue of the blood vessel wall 301 bulging toward the inside of the blood vessel 300. Hereinafter, the rugged pattern 304 is, for example, a lesion part formed by Monckeberg type medial calcification in which a middle coat of the blood vessel 300 is thickened through calcification.

In this case, flow of blood 400 is disturbed at the rugged pattern 304, and the blood 400 stagnates in the hollows (recesses) 302. The stagnation causes thrombus formation, and, depending on the extent of the thrombus formation, the blood vessel 300 may be plugged up.

In in FIGS. 2A to 4C, the left side is the upstream side with respect to the blood flow, and the right side is the downstream side. Accordingly, in the blood vessel 300, the blood 400 flows from the left side toward the right side in FIGS. 2A to 4C.

[1] Insertion Step

As depicted in FIG. 2B, the medical elongate body 1 in the state of being inserted in an outer tube 5 is inserted into the blood vessel 300 along a guide wire 6 which has preliminarily (previously) been inserted in the blood vessel 300. By this, the medical elongate body 1 and the outer tube 5 are inserted into the blood vessel 300 while being guided by the guide wire 6, so that the inserting operation can be carried out rather smoothly.

In this insertion step, the insertion is conducted until the jet balloon 32 inside the outer tube 5 reaches a position corresponding to the hollows 302 (recesses). For example, a contrast marker which is radiopaque is provided at an arbitrary position of a distal portion of the medical elongate body 1, and the inserting operation is performed under radioscopy, whereby positioning of the jet balloon 32 can be conducted easily. This allows the jet balloon (extension/expansion member) to be position in axially overlapping relation to the rugged pattern 304.

In a state in which the medical elongate body 1 is inserted in the outer tube 5, all of the distal-side balloon 31, the jet balloon 32 and the proximal-side balloon 33 are in a deflated state.

After the positioning is performed, the guide wire 6 may be withdrawn out of the blood vessel 300; alternatively, the subsequent steps may be conducted with the guide wire 6 kept indwelling in the blood vessel 300.

[2] Partitioning Step

Next, as depicted in FIG. 2C, the outer tube 5 is retracted proximally relative to the medical elongate body 1, to expose the distal-side balloon 31. In this instance, the jet balloon 32 and the proximal-side balloon 33 are kept accommodated in the outer tube 5.

Then, the contrast medium 100 as the working fluid is then supplied into the distal-side balloon 31 when the distal-side balloon 31 is in a deflated state (the deflated state is indicated by broken line in FIG. 2C), whereby the distal-side balloon 31 is brought into an inflated state as indicated by solid line in FIG. 2C. As a result, that part of the blood vessel 300 which is located on the upstream side of the hollows 302 is partitioned by the distal-side balloon 31. Therefore, the blood 400 is dammed up or stopped by the distal-side balloon 31.

Subsequently, as shown in FIG. 3A, the outer tube 5 is further retracted proximally relative to the medical elongate body 1, to expose the jet balloon 32 and the proximal-side balloon 33. Then, into the proximal-side balloon 33 being in a deflated state as indicated by broken line in FIG. 3B, the contrast medium 100 as the working fluid is supplied, whereby the proximal-side balloon 33 is put into an inflated state as indicated by solid line in FIG. 3B. By this, the blood vessel 300 is brought into a partition state in which the blood vessel 300 is partitioned on the forward and backward sides, namely, on the distal and proximal sides, of the hollows or recesses 302. In this partition state, that space S inside the blood vessel 300 which is located between the distal-side balloon 31 and the proximal-side balloon 33 is closed, so that the blood 400 is prevented from flowing into the space S. In other words, in the partition state, the blood flow is cut off in the space S.

As depicted in FIGS. 3A and 3B, in the partitioning step, the jet balloon 32 is put in an inflated state (i.e., is inflated) due to the expansion of the net-like body 41. In this instance, the jet balloon 32 is inflated while remaining in a roughly cylindrical shape according to the shape of the net-like body 41. In addition, in the inflated state, the jet balloon 32 or the net-like body 41 is in contact with crest portions 303 of the rugged pattern 304, and is restrained from further inflation.

Since the contrast medium 100 is used as the working fluid for the distal-side balloon 31 and the proximal-side balloon 33, the partitioning step can be performed under radioscopy. Therefore, the operator can securely grasp the fact that the partition state has been attained through the inflation of the distal-side balloon 31 and the proximal-side balloon 33.

[3] Filling Step

In this contact state, the gel 200 is supplied into the jet balloon 32, and, when the pressure inside the jet balloon 32 has exceeded a predetermined value, the gel 200 is jetted out through the jet ports 321 (see FIG. 3C). As a result, the hollows or recesses 302 in the blood vessel inner wall are filled up with the gel 200.

Here, in a case where the net-like body 41 is omitted, or in a case where the inflation limit of the jet balloon 32 is not restricted, the flexible jet balloon 32 in the inflated state is deformed to enter into the hollows or recesses 302 in such a manner that its outside diameter conforms to the rugged pattern 304. In this entered state, it is difficult to jet the gel 200 into the hollows or recesses 302 to fill up the hollows 302 with the gel 200.

On the other hand, in the medical elongate body 1, the inflation limit of the jet balloon 32 is restricted by the net-like body 41. In the inflated state, therefore, a gap is formed between the jet port formed portion 322 Outer surface of the jet port formed portion) and the inner surfaces of the hollows 302, and it is possible to jet out the gel 200 into the gap and thereby to fill up the hollows 302 with the gel 200.

In addition, the jet balloon 32 is controlled in shape by the net-like body 41. Specifically, an outer circumference portion of a longitudinal cross-sectional shape of the jet balloon 32 is restricted to be rectilinear in shape along the longitudinal direction of the medical elongate body 1. As a result, it is possible to smoothen the surface of the gel 200 with which the hollows 302 are filled up.

[4] Withdrawing Step

Next, as illustrated in FIG. 4A, the distal-side balloon 31 and the proximal-side balloon 33 are deflated. By this, the partition state is canceled. That is, the blood vessel is no longer partitioned. In this instance, the gel 200 remains filling up the hollows 302. Then, the jet balloon 32 is deflated.

In addition, the deflation in this step is conducted by drawing the working fluid out of the distal-side balloon 31, the jet balloon 32 and the proximal-side balloon 33.

Then, as depicted in FIG. 4B, the medical elongate body 1 is retracted proximally relative to the outer tube 5, whereby the distal-side balloon 31, the jet balloon 32 and the proximal-side balloon 33 are accommodated into the outer tube 5.

Finally, the medical elongate body 1 and the outer tube 5 are withdrawn proximally out of the blood vessel 300, followed by a predetermined treatment.

In this withdrawing step, the distal-side balloon 31, the jet balloon 32 and the proximal-side balloon 33 may be deflated simultaneously or may be deflated at different timings.

According to the filling method of the present disclosure as described above, the hollows 302 in the blood vessel 300 can be selectively filled with the gel 200, and the rugged pattern 304 can be smoothened, as illustrated in FIG. 4C. By this, stagnation of the blood 400 in the hollows 302 as depicted in FIG. 2A can be prevented from occurring, and smooth blood flow can be secured. Therefore, it is possible to prevent the occurrence of a situation in which a thrombus is formed due to stagnation of the blood 400 to plug up the blood vessel 300 or a situation wherein the cross-sectional area of that part of the blood vessel 300 through which the blood 400 passes is reduced excessively.

In the above description, the filling method of the present disclosure has been explained while showing the rugged pattern arising from medial calcification as an example. According to the filling method of the present disclosure, however, it is also possible to similarly smoothen a rugged pattern due to a thrombus generated on a blood vessel wall, a rugged pattern arising from arterial sclerosis, a rugged pattern due to a plaque which is a macular hypertrophic lesion of an inner membrane present at a focus of arterial sclerosis, etc.

In the filling method of the present disclosure, the jetting of the gel 200 is conducted in the state in which the blood flow in that portion of the blood vessel 300 where the hollows 302 are formed is cut off. This ensures that the jetted gel 200 can be prevented from being washed away by the blood 400. Accordingly, the hollows 302 can be filled up with the gel 200 reliably.

Further, the filling method of the present disclosure is effective for treatment in a lower limb region. The lower limb region is susceptible to the formation of a rugged pattern at the blood vessel wall due to medial calcification. When formation of a thrombus due to such a rugged pattern is prevented, it is possible to stop a cascade of organization, inflammation or intimal thickening.

<Second Embodiment>

Figure 5:
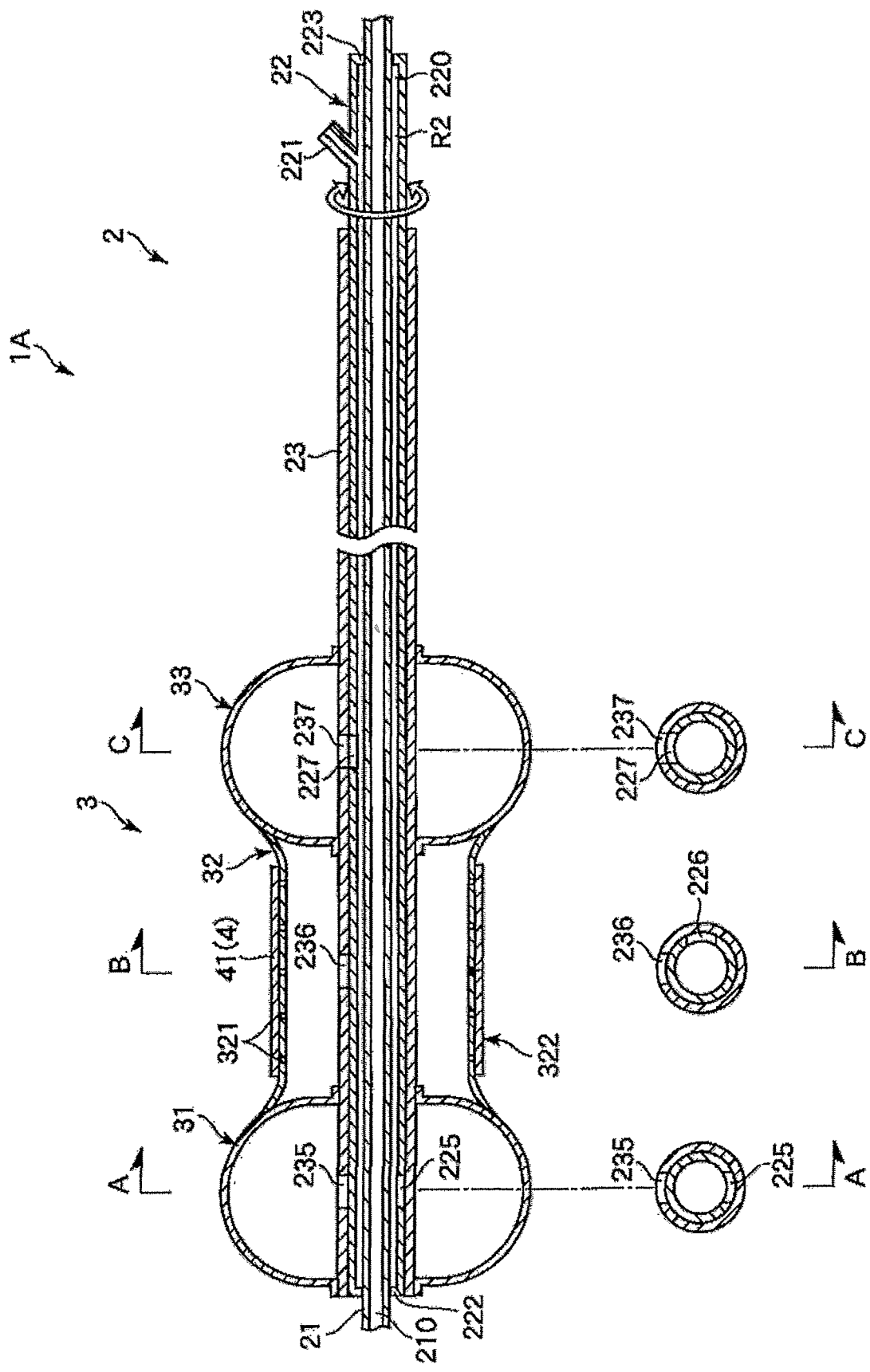
FIG. 5 is a longitudinal cross-sectional view showing a second embodiment of the medical elongate body according to the present disclosure.

FIG. 5 is a longitudinal cross-sectional view showing a second embodiment of the medical elongate body according to the present disclosure Representing another example of the inventive medical elongate body disclosed here. FIGS. 6A to 6C illustrate a state in which a distal-side balloon of the medical elongate body shown in FIG. 5 is being inflated, wherein FIG. 6A is a cross-sectional view taken along the section line A-A of FIG. 5, FIG. 6B is a cross-sectional view taken along the section line B-B of FIG. 5, and FIG. 6C is a cross-sectional view taken along the section line C-C of FIG. 5. FIGS. 7A to 7C illustrate a state in which a jet balloon section of the medical elongate body shown in FIG. 5 is being inflated, wherein FIG. 7A is a cross-sectional view taken along the section line A-A of FIG. 5, FIG. 7B is a cross-sectional view taken along the section line B-B of FIG. 5, and FIG. 7C is a cross-sectional view taken along the section line C-C of FIG. 5. FIGS. 8A to 8C illustrate a state in which a proximal-side balloon section of the medical elongate body shown in FIG. 5 is being inflated, wherein FIG. 8A is a cross-sectional view taken along the section line A-A of FIG. 5, FIG. 8B is a cross-sectional view taken along the section line B-B of FIG. 5, and FIG. 8C is a cross-sectional view taken along the section line 8C-8C of FIG. 5.

In FIGS. 6A to 8C, a first catheter 21 is omitted from the drawing, and only a second catheter 22 and a third catheter 23 are illustrated.

Referring to these figures, the second embodiment of the filling method and the medical elongate body according to the present disclosure will be described below. The following description will be made primarily of differences from the above-described first embodiment, and descriptions of the same items as above will be omitted.

This embodiment is the same as the first embodiment above, except for differences in the configuration of the catheter body.

As illustrated in FIG. 5, in a medical elongate body 1A, a catheter body 2 has a triple tube structure including the first catheter 21, the second catheter 22, and the third catheter 23. The first catheter 21, the second catheter 22 and the third catheter 23 are arranged concentrically in this order from inside.

Like in the first embodiment, in the medical elongate body 1A, a space between the first catheter 21 and the second catheter 22 functions as a passage R2.

In addition, an outer circumference portion of the second catheter 22 and an inner circumference portion of the third catheter 23 are in close contact with each other. The second catheter 22 is configured to be rotatable about a center axis of the medical elongate body 1A, relative to the first catheter 21 and the third catheter 23.

The second catheter 22 is provided with a through-hole 225, a through-hole 226 and a through-hole 227 which penetrate its tube wall in the thickness direction of the tube wall. The through-hole 225, the through-hole 226 and the through-hole 227 are formed at positions shifted from one another along the longitudinal direction of the medical elongate body 1A.

The position of the through-hole 225 in the longitudinal direction of the medical elongate body 1A is the same as that of a distal-side balloon 31. The position of the through-hole 226 in the longitudinal direction of the medical elongate body 1A is the same as that of a jet balloon 32. The position of the through-hole 227 in the longitudinal direction of the medical elongate body 1A is the same as that of a proximal-side balloon 33.

In addition, the through-hole 225, the through-hole 226 and the through-hole 227 are located at positions shifted from one another in the circumferential direction of the medical elongate body 1A. In this embodiment, the positions of the through-hole 225, the through-hole 226 and the through-hole 227 are shifted by approximately 90° each in the circumferential (rotational) direction of the medical elongate body 1A.

The third catheter 23 is shorter than the second catheter 22, and the position of the distal end of the third catheter 23 is the same as that of the second catheter 22. The third catheter 23 is provided with the distal-side balloon 31 and the proximal-side balloon 33 spaced apart from each other along the longitudinal direction of the medical elongate body 1A. In this embodiment, the jet balloon 32 has its distal portion joined to the distal-side balloon 31, and has its proximal portion joined to the proximal-side balloon 33.

In addition, the third catheter 23 is provided with a through-hole 235, a through-hole 236, and a through-hole 237 which to penetrate its tube wall in the thickness direction of the tube wall. The through-hole 235, the through-hole 236 and the through-hole 237 are formed at positions shifted from one another along the longitudinal direction of the medical elongate body 1A.

The through-hole 235 is the same as the through-hole 225 in the position in the longitudinal direction of the medical elongate body 1A. The through-hole 236 is the same as the through-hole 226 in the position in the longitudinal direction of the medical elongate body 1A. The through-hole 237 is the same as the through-hole 227 in the position in the longitudinal direction of the medical elongate body 1A.

The through-hole 235, the through-hole 236 and the through-hole 237 are the same in the position in the circumferential direction of the medical elongate body 1A.

In the medical elongate body 1A configured as above, by rotating the second catheter 22, it is possible to switch between a first communication state in which the through-hole 225 and the through-hole 235 communicate with each other, a second communication state in which the through-hole 226 and the through-hole 236 communicate with each other, and a third communication state in which the through-hole 227 and the through-hole 237 communicate with each other. In the first communication state, a working fluid can be supplied into the distal-side balloon 31. In the second communication state, a working fluid can be supplied into the jet balloon 32. In the third communication state, a working fluid can be supplied into the proximal-side balloon 33.

FIGS. 6A to 6C illustrate the first communication state. As depicted in FIG. 6A, in the first communication state, the through-hole 225 and the through-hole 235 communicate with each other. As a result, the passage R2 and the distal-side balloon 31 communicate with each other, so that the working fluid can be supplied into the distal-side balloon 31.

In addition, as shown in FIG. 6B, in the first communication state, the through-hole 226 and the through-hole 236 are positionally shifted from each other in the circumferential (rotational) direction of the medical elongate body 1A and, therefore, do not communicate with each other. For this reason, in the first communication state, the working fluid can be prevented from being supplied into the jet balloon 32.

As illustrated in FIG. 6C, in the first communication state, the through-hole 227 and the through-hole 237 do not communicate with each other, since their positions are shifted from each other in the circumferential direction of the medical elongate body 1A. This ensures that in the first communication state, the working fluid can be prevented from being supplied into the proximal-side balloon 33.

FIGS. 7A to 7C illustrate the second communication state. As shown in FIG. 7A, in the second communication state, the through-hole 225 and the through-hole 235 are positionally shifted (rotationally shifted) from each other in the circumferential direction of the medical elongate body 1A and, therefore, do not communicate with each other. In the second communication state, therefore, supply of the working fluid into the distal-side balloon 31 is prevented from occurring.

As depicted in FIG. 7B, in the second communication state, the through-hole 226 and the through-hole 236 communicate with each other. For this reason, the passage R2 and the jet balloon 32 communicate with each other, so that the working fluid, or the gel 200 can be supplied into the jet balloon 32.

In addition, as shown in FIG. 7C, in the second communication state, the through-hole 227 and the through-hole 237 do not communicate with each other, since their positions are rotationally shifted from each other in the circumferential direction of the medical elongate body 1A. In the second communication state, therefore, the working fluid can be prevented from being supplied into the proximal-side balloon 33.

FIGS. 8A to 8C illustrate the third communication state. As depicted in FIG. 8A, in the third communication state, the through-hole 225 and the through-hole 235 are positionally shifted (rotationally shifted) from each other in the circumferential direction of the medical elongate body 1A and, therefore, do not communicate with each other. This ensures that in the third communication state, supply of the working fluid into the distal-side balloon 31 can be prevented from occurring.

As shown in FIG. 8B, in the third communication state, the through-hole 226 and the through-hole 236 do not communicate with each other, as their positions are shifted from each other in the circumferential direction of the medical elongate body 1A. For this reason, in the third communication state, supply of the working fluid into the jet balloon 32 can be prevented from occurring.

As depicted in FIG. 8C, in the third communication state, the through-hole 227 and the through-hole 237 communicate with each other. Therefore, the passage R2 and the proximal-side balloon 33 communicate with each other, so that the working fluid can be supplied into the proximal-side balloon 33.

In this way, the medical elongate body 1A can be said to have a switching mechanism for switching between the first communication state, the second communication state and the third communication state by rotating operations. In this embodiment, such switching between the first communication state, the second communication state and the third communication state can be performed by a simple method of rotating the second catheter 22.

Further, according to the medical elongate body 1A, a fourth catheter 24 can be omitted, and a reduction in the thickness (diametric size) of the medical elongate body 1A can be realized accordingly.

A marker indicative of an amount of rotation, or an angle of rotation, of the second catheter 22 may be imparted to a proximal portion of the second catheter 22 or a proximal portion of the third catheter 23. By this, the switching operations can be performed easily and swiftly.

Further, the switching operations as above may be conducted in a state where the pressure inside the passage R2 is raised by supplying, for example, a working fluid into the passage R2. In this case, when one of the first communication state, the second communication state and the third communication state is established, the working fluid is supplied into one of the distal-side balloon 31, the jet balloon 32 and the proximal-side balloon 33, resulting in a lowering in the internal pressure. Based on the lowering in the internal pressure, it is possible to grasp or know (be informed about) the state in which the desired pair of through-holes communicate with each other.

The method of using the medical elongate body 1A thus configured, or the filling method, is roughly the same as that in the first embodiment and, therefore, detailed description thereof is omitted here.

In this embodiment, in [2] the partitioning step, the above-mentioned switching operations are conducted, wherein the distal-side balloon 31, the proximal-side balloon 33 and the jet balloon 32 are inflated in this order, in the same manner as in the first embodiment. In other words, the first communication state, the third communication state and the second communication state are switchedly established in this order.

In addition, at the time of switching from the third communication state to the second communication state, or at the time of switching the working fluid from the contrast medium 100 to the gel 200, the inside of the passage R2 may be washed. After the passage R2 is washed and before the gel 200 is supplied, the jet balloon 32 may be inflated by, for example, physiological saline solution and the physiological saline solution may be jetted out from the jet balloon 32. By such a procedure, the inside of the blood vessel can be cleaned prior to filling with the gel 200.

The through-hole 225, the through-hole 226, the through-hole 227, the through-hole 235, the through-hole 236, and the through-hole 237 may be each provided in pluralities.

That is, more than one of each of the trough-holes 225, 226, 227, 235, 236, 237 may be provided.

<Third Embodiment>

Figure 9:
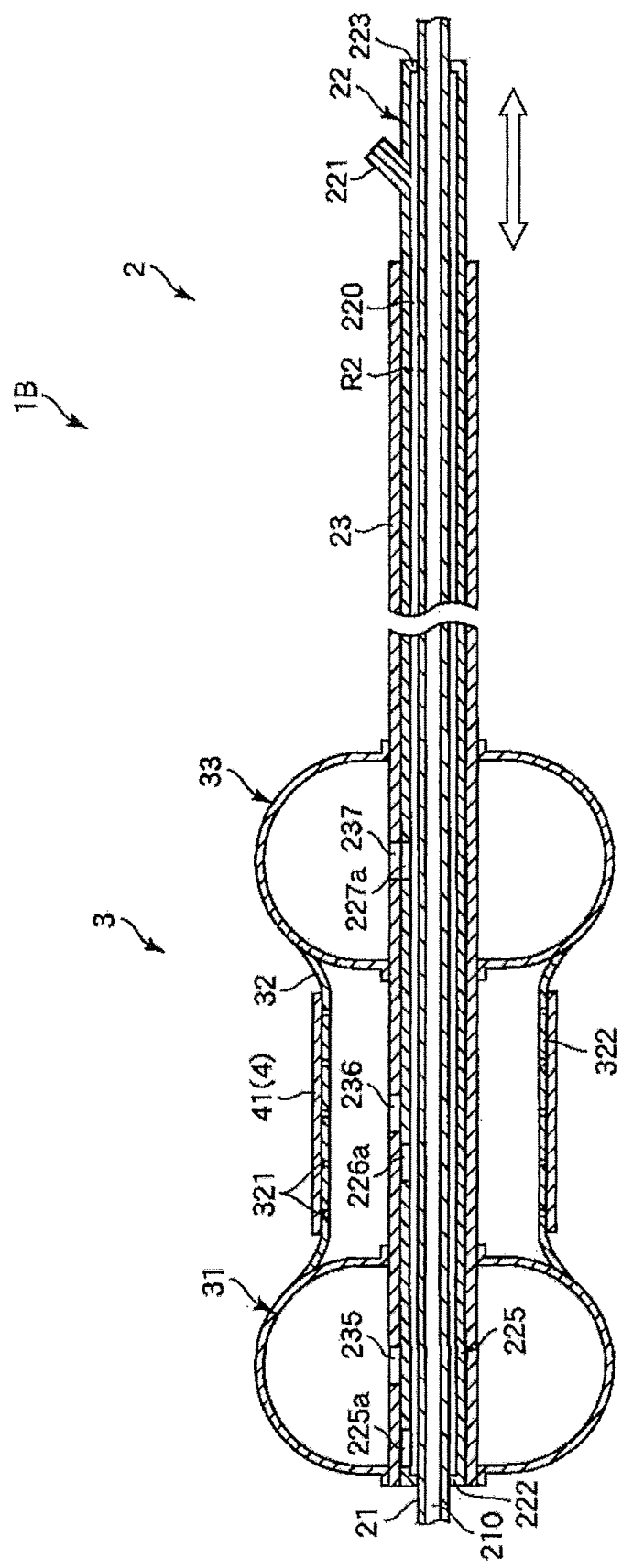
FIG. 9 is a longitudinal cross-sectional view showing a third embodiment of the medical elongate body according to the present disclosure.
Figure 10A:
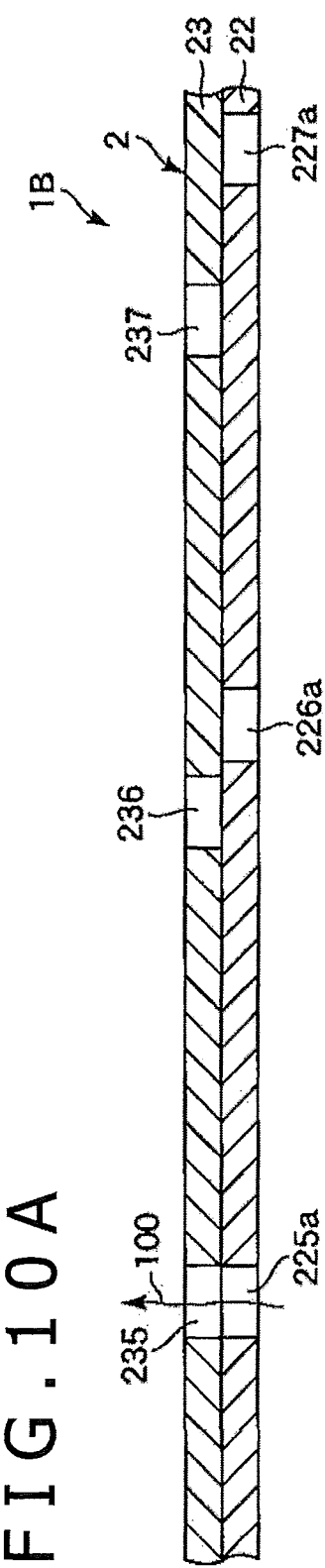
Figure 10B:
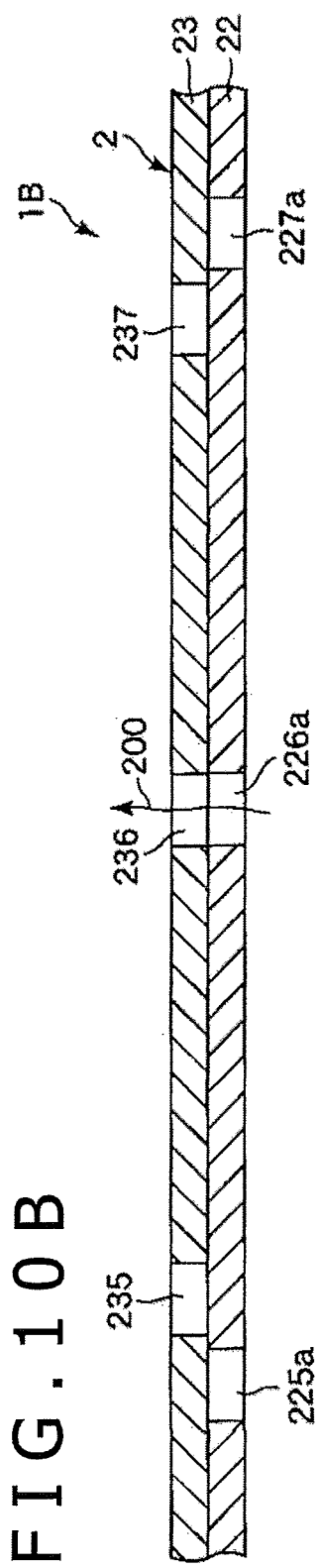
Figure 10C:
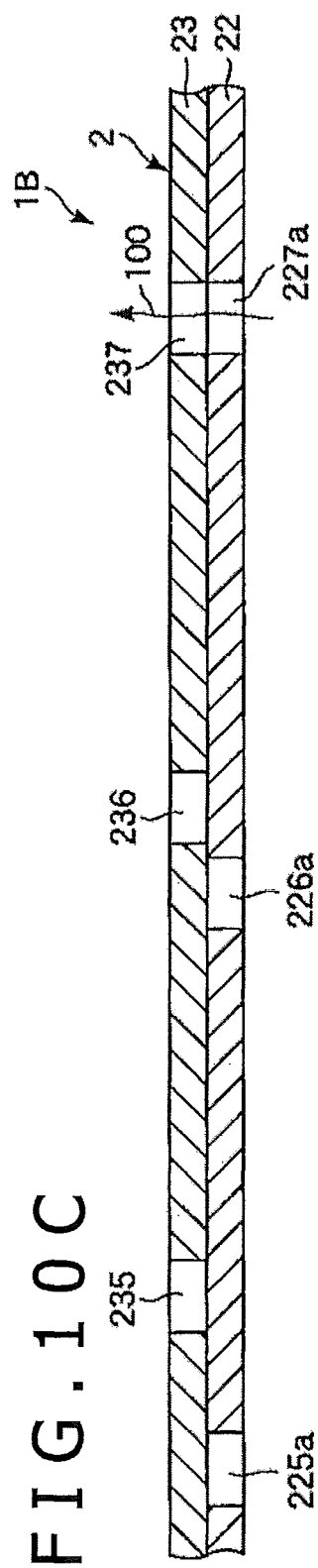

FIG. 9 is a longitudinal cross-sectional view showing a third embodiment of the medical elongate body according to the present disclosure. FIGS. 10A to 10C are enlarged longitudinal cross-sectional views of a distal portion of a catheter body of the medical elongate body shown in FIG. 9, wherein FIG. 10A illustrates a first communication state, FIG. 10B illustrates a second communication state, and FIG. 10C illustrates a third communication state.

Referring to these figures, the third embodiment of the filling method and the medical elongate body according to the present disclosure will be described below. The following description will focus primarily on differences from the above-described embodiments, and a detailed description of features already described above will not be repeated.

This embodiment is the same as the second embodiment above, except for differences in the configuration of the switching mechanism.

As shown in FIG. 9, in a medical elongate body 1B in this embodiment, a second catheter 22 has a through-hole 225a, a through-hole 226a and a through-hole 227a which are provided in its distal portion and formed to penetrate its tube wall in the thickness direction of the tube wall. The through-hole 225a, the through-hole 226a and the through-hole 227a are disposed at positions shifted from one another along the longitudinal direction of the second catheter 22. The through-hole 225a, the through-hole 226a and the through-hole 227a are the same in the position in the circumferential direction of a catheter body 2.

In addition, the separated distance between the through-hole 225a and the through-hole 226a is equal to the separated distance between the through-hole 226a and the through-hole 227a. The separated distance between the through-hole 225a and the through-hole 226a is greater than the separated distance between a through-hole 235 and a through-hole 236 in a third catheter 23. The separated distance between the through-hole 226a and the through-hole 227a is greater than the separated distance between the through-hole 236 and a through-hole 237 in the third catheter 23.

In this embodiment, the second catheter 22 is configured to be slidable, or movable, in the longitudinal direction of the second catheter 22 relative to the third catheter 23.

In the medical elongate body 1B, like in the second embodiment, it is possible to switch between a first communication state in which the through-hole 225a and the through-hole 235 communicate with each other (see FIG. 10A), a second communication state in which the through-hole 226a and the through-hole 236 communicate with each other (see FIG. 10B), and a third communication state in which the through-hole 227a and the through-hole 237 communicate with each other (see FIG. 10C), by sliding the second catheter 22 relative to the third catheter 23.

Thus, the medical elongate body 1B has a switching mechanism for switching between the first communication state, the second communication state and the third communication state by sliding operations. In addition, in the medical elongate body 1B, the switching between the first communication state, the second communication state and the third communication state can be carried out by a simple method of sliding the second catheter 22 relative to the third catheter 23.

In this embodiment, the second catheter 22 may be configured to be rotatable relative to the third catheter 23. For example, in the process of transition from the first communication state depicted in FIG. 10A to the third communication state shown in FIG. 10C, if the second catheter 22 is gradually slid, the through-hole 226a and the through-hole 236 would temporarily communicate with each other. In this case, when a rotating operation is conducted to rotate the second catheter 22 in such a manner that the position of the through-hole 226a in the circumferential direction is deviated from that of the through-hole 236, the just-mentioned temporary communication can be prevented from occurring.

<Fourth Embodiment>

Figure 11:
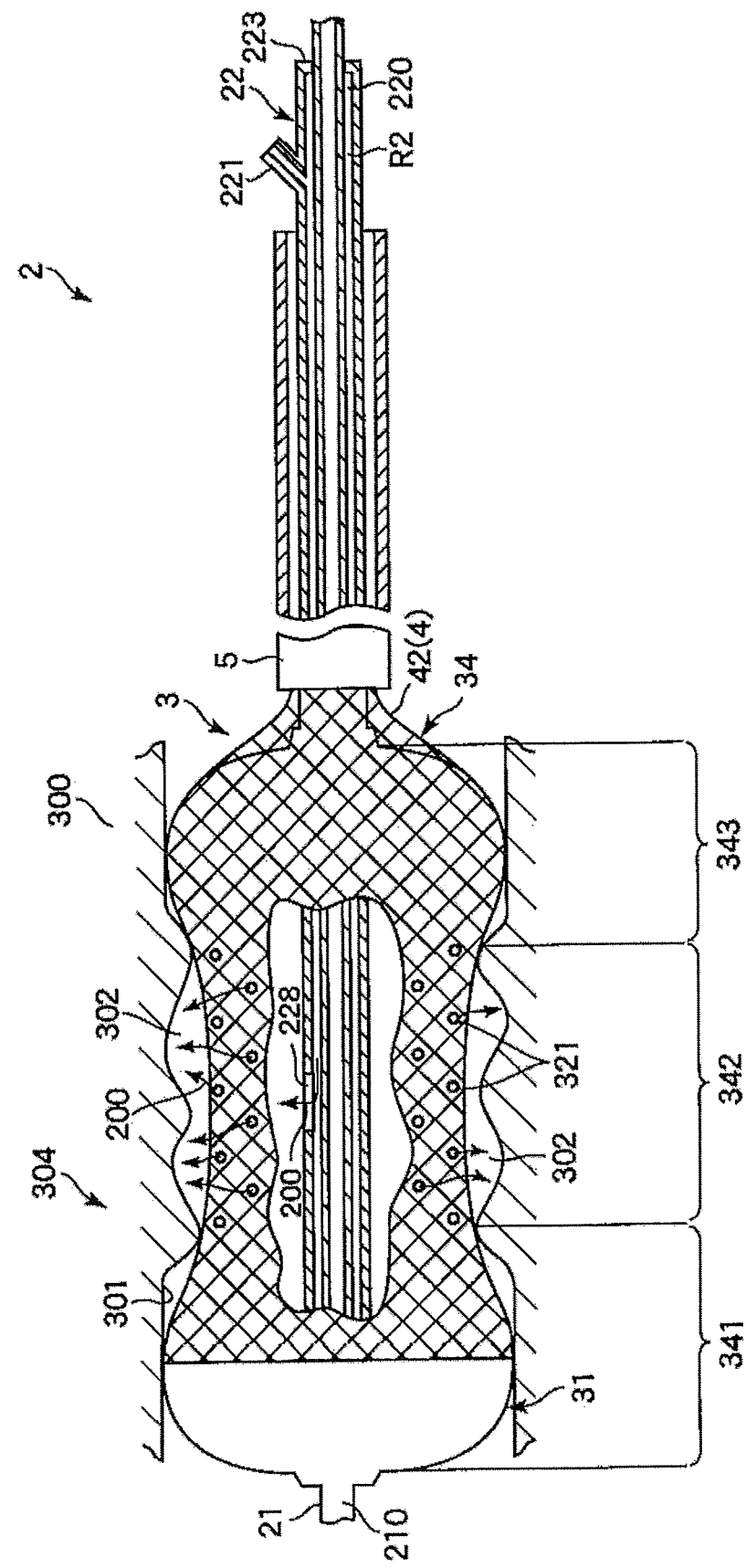
FIG. 11 is a partial longitudinal cross-sectional view showing a fourth embodiment of the medical elongate body according to the present disclosure.

FIG. 11 is a partial longitudinal cross-sectional view showing a fourth embodiment of the medical elongate body according to the present disclosure.

Referring to this figure, the fourth embodiment of the filling method and the medical elongate body according to the present disclosure will be described below. The following description focuses primarily on the differences relative to the above-described embodiments, and a detailed description of features already described above will not be repeated.

This embodiment is the same as the first embodiment above, except for differences in the configurations of the balloon unit and the restricting section.

As illustrated in FIG. 11, a medical elongate body 1C has a configuration wherein the third catheter 23 and the fourth catheter 24 in the first embodiment are omitted, and an outer tube 5 is further provided.

In addition, a second catheter 22 is provided in its distal portion with a through-hole 228 which penetrates its tube wall in the thickness direction of the tube wall. The through-hole 228 functions as a supply port for supplying a gel 200 into a balloon 34 (described later) via a passage R2.

As depicted in FIG. 11, the medical elongate body 1C has the balloon 34 provided at a distal portion of the second catheter 22. The balloon 34 is elongated in shape. In addition, the balloon 34 is provided with a plurality of jet ports 321 in an intermediate portion in the longitudinal direction thereof.

In this embodiment, a restricting section 4 has a net-like body (net body) 42. The net-like body 42 has a self-expanding property. In other words, the net-like body 42 has a biasing force for biasing the net-like body 42 in the direction for expanding, in its contracted state. The net-like body 42 has its proximal portion inserted in the outer tube 5, and has its distal portion located in the vicinity of a distal portion of the balloon 34. Specifically, the net-like body 42 covers the balloon 34 up to a proximal end of the balloon 34, exclusive of a part of a distal portion of the balloon 34. In addition, in this embodiment, the net-like body 42 is fixed to an outer circumference portion of the balloon 34.

The net-like body 42 in its expanded state has such a shape that its intermediate portion in its longitudinal direction is gently hollowed to the inside (i.e., recessed radially inwardly to define a concave shape). Therefore, as shown in FIG. 11, the balloon 34 in its inflated state is sectioned into a distal region 341 located on the distal side, a proximal region 343 located on the proximal side, and an intermediate region 342 located therebetween. The distal region 341 and the proximal region 343 are substantially the same in outside diameter, and are greater in outside diameter than the intermediate region 342. The intermediate region 342 is a jet port formed portion where jet ports 321 are formed.

In this embodiment, when the distal region 341 is exposed, starting from a state in which the balloon 34 and the net-like body 42 are accommodated in the outer tube 5 and expansion of the net-like body 42 is thereby restricted, the distal region 341 is inflated by being pulled by the net-like body 42. This applies also to the proximal region 343. This ensures that when the balloon 34 is exposed from the outer tube 5, a partition state is established, even without supply of the working fluid. Therefore, simplification of [2] the partitioning step can be realized.

In addition, in the partition state, the intermediate region 342 also has already been inflated, as depicted in FIG. 11. The intermediate region 342 in its inflated state has an external shape which is restricted to a roughly cylindrical shape. This makes it possible to supply the gel 200 into the balloon 34, to jet out the gel 200 through the jet ports 321, and thereby to fill up hollows or recesses 302 with the gel 200.

In this embodiment, in [2] the partitioning step, the distal region 341 may be exposed and inflated, followed by exposing and inflating the proximal region 343, or the distal region 341 and the proximal region 343 may be exposed and inflated substantially simultaneously.

In the latter case, if a configuration is adopted in which the distal region 341 is inflated earlier than the proximal region 343, partitioning can be conducted starting from the upstream side. Such a configuration can be realized, for example, by making the proximal region 343 of the balloon 34 greater in film thickness than the distal region 341 such that the proximal region 343 is less liable to inflate following up to the net-like body 42 than the distal region 341.

In this embodiment, the distal region 341 constitutes a distal-side balloon section, the intermediate region 342 constitutes a jet balloon section, and the proximal region 343 constitutes a proximal-side balloon section. In other words, in this embodiment, the distal-side balloon section, the jet balloon section and the proximal-side balloon section can be said to be formed integrally.

<Fifth Embodiment>

Figure 12:
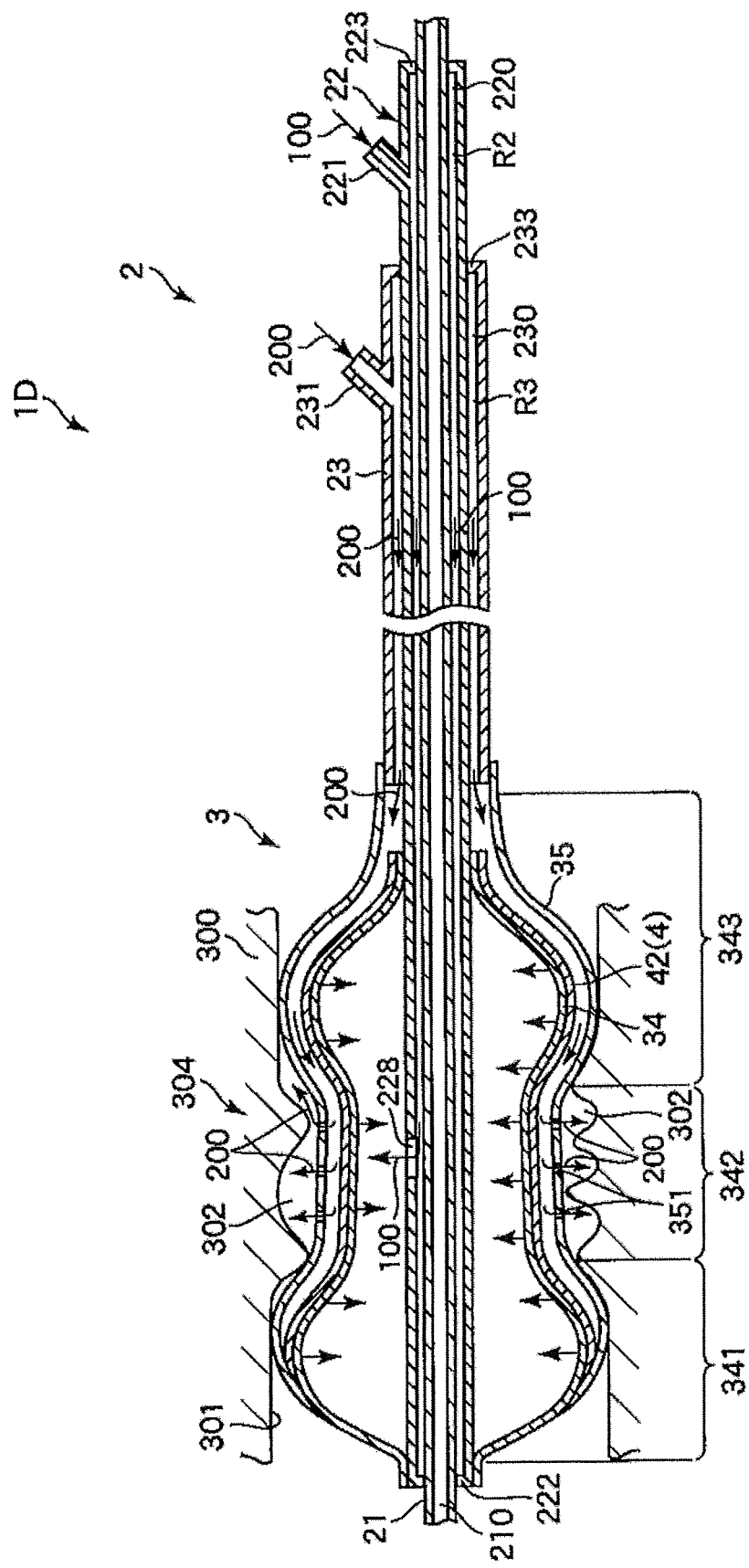
FIG. 12 is a longitudinal cross-sectional view showing a fifth embodiment of the medical elongate body according to the present disclosure.

FIG. 12 is a longitudinal cross-sectional view showing a fifth embodiment of the medical elongate body according to the present disclosure.

Referring to this figure, the fifth embodiment of the filling method and the medical elongate body according to the present disclosure will be described below. The following description will focus primarily on differences between this embodiment and the above-described embodiments, and a detailed description of features already described above will not be repeated.

This embodiment is the same as the fourth embodiment above, except that the medical elongate body in this embodiment has an outer balloon.

As illustrated in FIG. 12, in a medical elongate body 1D, a catheter body 2 has a triple tube structure including a first catheter 21, a second catheter 22, and a third catheter 23.

A passage R3 between the second catheter 22 and the third catheter 23 in this embodiment functions as a passage through which a gel 200 passes.

As depicted in FIG. 12, in the medical elongate body 1D, a balloon unit 3 is a double balloon including a balloon 34 as an inner balloon, and an outer balloon 35 provided on an outer circumference side of the balloon 34.

The outer balloon 35 is elongated in shape, and its proximal portion is fixed to a distal outer circumference portion of the third catheter 23. In addition, a distal portion of the outer balloon 35 is fixed to a distal region 341 of the balloon 34. In other words, the outer balloon 35 has a configuration in which it covers the balloon 34 in a range from an intermediate portion of the distal region 341 to the proximal end of the balloon 34.

The outer balloon 35 is inflated in such a manner that a general shape in an inflated state of the outer balloon 35 conforms to the shape of the balloon 34. Specifically, the outer balloon 35 has a shape in which an intermediate portion in the longitudinal direction of the outer balloon 35 is hollowed to the inside or recessed radially inwardly, and the hollowed portion is located on the outside of an intermediate region 342 of the balloon 34.

In addition, that portion of the outer balloon 35 which corresponding to the intermediate region 342 of the balloon 34 is provided with a plurality of jet ports 351 which penetrate the outer balloon 35 in the film thickness direction. By this, the gel 200 flowing downstream in the passage R3 flows downstream between the balloon 34 and the outer balloon 35, and is jetted to the outside through the jet ports 351.

In in this embodiment, a net-like body 42 is located between the balloon 34 and the outer balloon 35, and restricts a limit of inflation of the balloon 34. The net-like body 42 is fixed to an outer circumference portion of the balloon 34.

The medical elongate body 1D as above has the following advantages.

Since the balloon 34 has a limit of inflation restricted by the net-like body 42 at its intermediate region 342, the balloon 34 can be prevented from forcing open to the outside that portion of the outer balloon 35 which is hollowed to the inside. Therefore, the limit of inflation of the outer balloon 35 is restricted at the intermediate portion 342, so that the hollows or recesses 302 can be filled up with the gel 200.

In [3] a filling step, in an inflated state of the balloon unit 3, the balloon 34 is biased by the net-like body 42 in a direction for deflating to the inside, or in the direction of arrows in FIG. 12. For this reason, when the gel 200 flows downstream between the balloon 34 and the outer balloon 35, the balloon 34 is prevented from compressing the gel 200 to hamper the flowing-downstream of the gel 200.

Further, in this embodiment, the outer tube 5 used in the fourth embodiment is omitted. In [1] an insertion step, by applying suction applied through a side port 221 and a side port 231 in such a manner as to apply a negative pressure to the inside of the balloon 34 and the outer balloon 35, the balloon 34 and the outer balloon 35 can be carried while their deflated states are maintained reliably. As a result, the medical elongate body 1D can be smoothly carried within a comparatively thin blood vessel by omitting the outer tube 5.

While the filling method and the medical elongate body disclosed here have been described above based on embodiments representing examples of the inventive medical elongate body and method disclosed here, the present disclosure is not limited to the disclosed embodiments. The configurations of components and the steps employed can be replaced by others having the same or equivalent functions to those of the original ones. Other arbitrary structures or steps may also be added to the ones according to the present disclosure.

The present disclosure can also be applied, for example, to treatment of aneurysm. In this case, the aneurysm formed by hollowing or recessing a blood vessel wall toward the outside of a blood vessel is filled up with a gel. By this, while occluding the aneurysm with the gel, a rugged pattern of the blood vessel wall formed due to the aneurysm can be smoothened.

In addition, while the net-like body as a restricting section has been provided on the outside of the balloon in each of the above-described embodiments, the present disclosure is not limited to this configuration. For example, the net-like body may be provided on the inside of the balloon, or may be embedded at an intermediate position in the film thickness direction of the balloon.

While a case wherein the medical elongate body is delivered from the downstream side toward the upstream side with respect to the blood flow, then the blood flow is stopped in the order of the upstream side and the downstream side, and the hollows or recesses are thereby filled up with the gel has been described in the filling step in the above embodiments, the present disclosure is not limited to this configuration. For example, in relation to hollows formed in a blood vessel wall, the medical elongate body may not only be delivered from the downstream side toward the upstream side with respect to the blood flow but also be delivered in the reverse direction, or along the blood flow direction. In this case, the hollows may be filled up with the gel by stopping the blood flow on the downstream side and then on the upstream side.

While a case wherein thrombus formation has occurred in a rectilinear blood vessel has been described in the above embodiments, the present disclosure is not limited to this configuration. For example, the present disclosure can also be applied to a case where thrombus formation has occurred in a curved blood vessel.

The blood vessel lumen forming method and the medical elongated body according to the described aspects of the present disclosure will be described in detail below, with reference to preferred embodiments thereof illustrated in the accompanying drawings.

<Sixth Embodiment>

Figure 13:
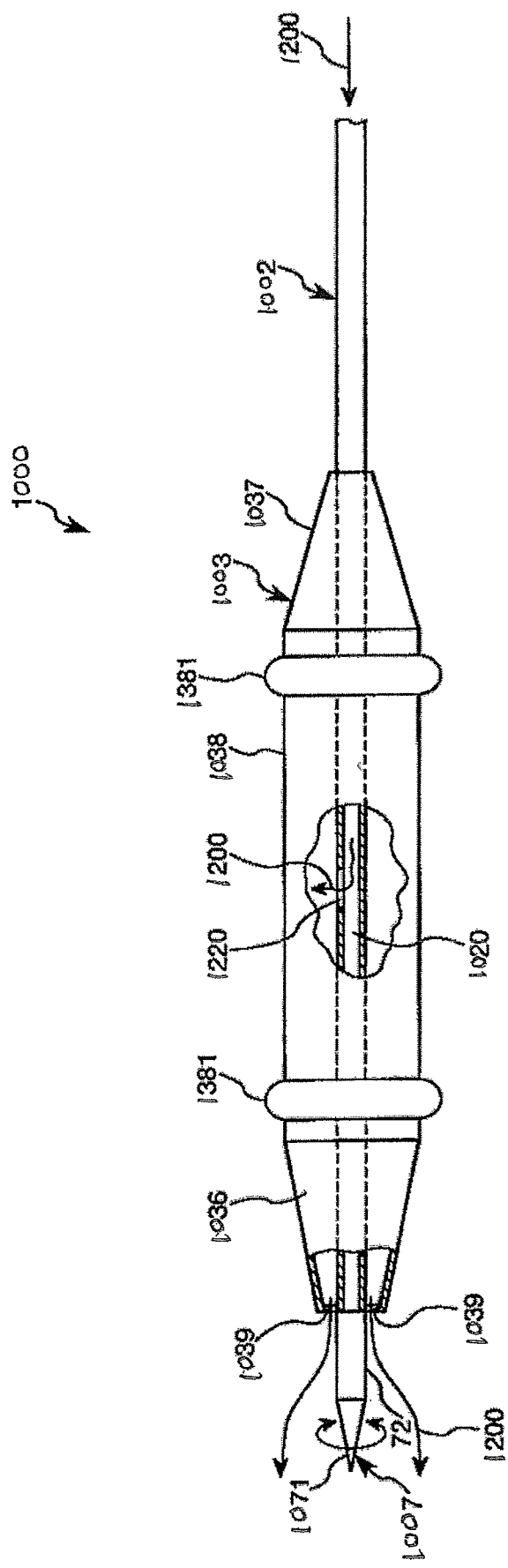
FIG. 13 is a partially sectional longitudinal view illustrating a sixth embodiment of the medical elongated body according to the present disclosure.
Figure 14A:
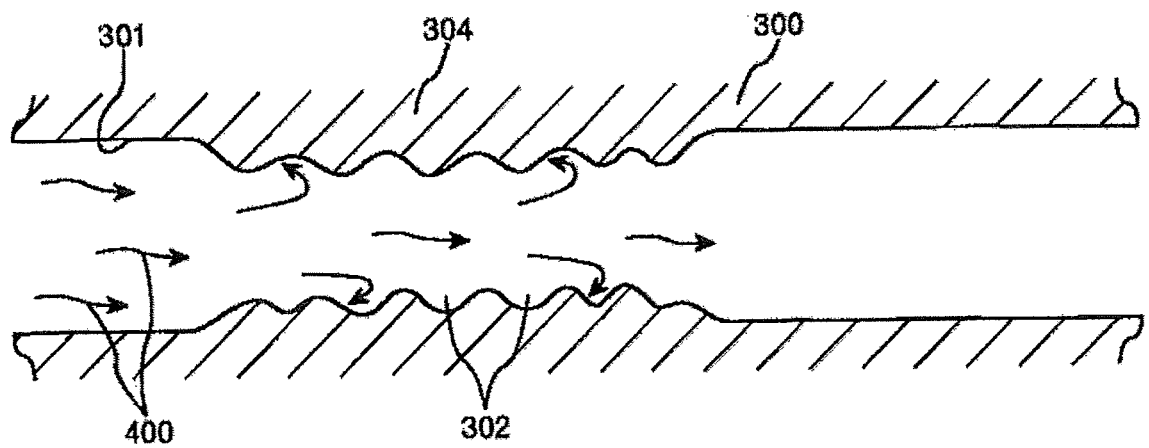
Figure 14B:
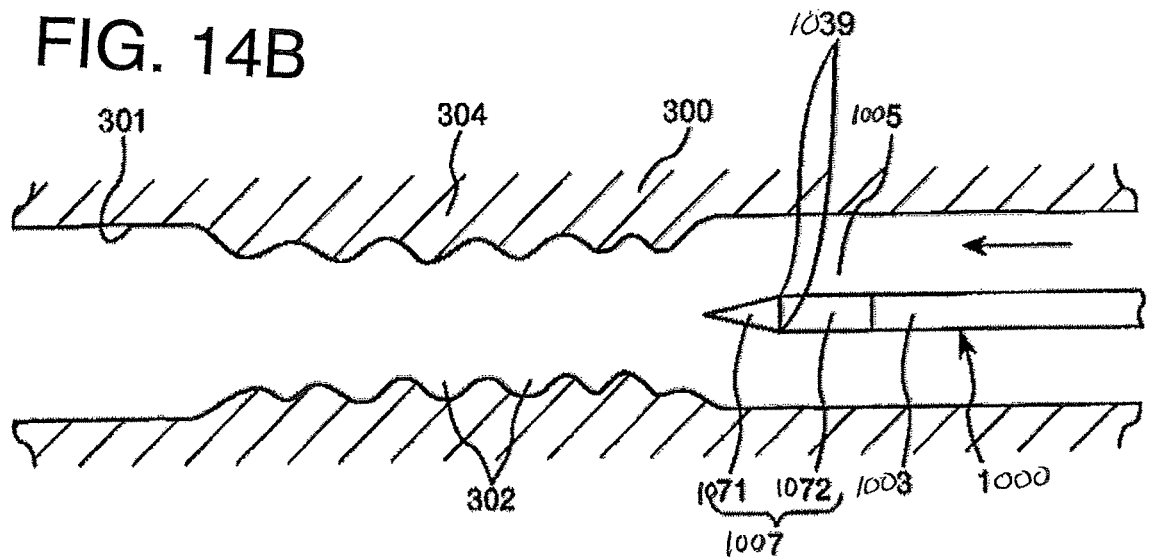
Figure 14C:
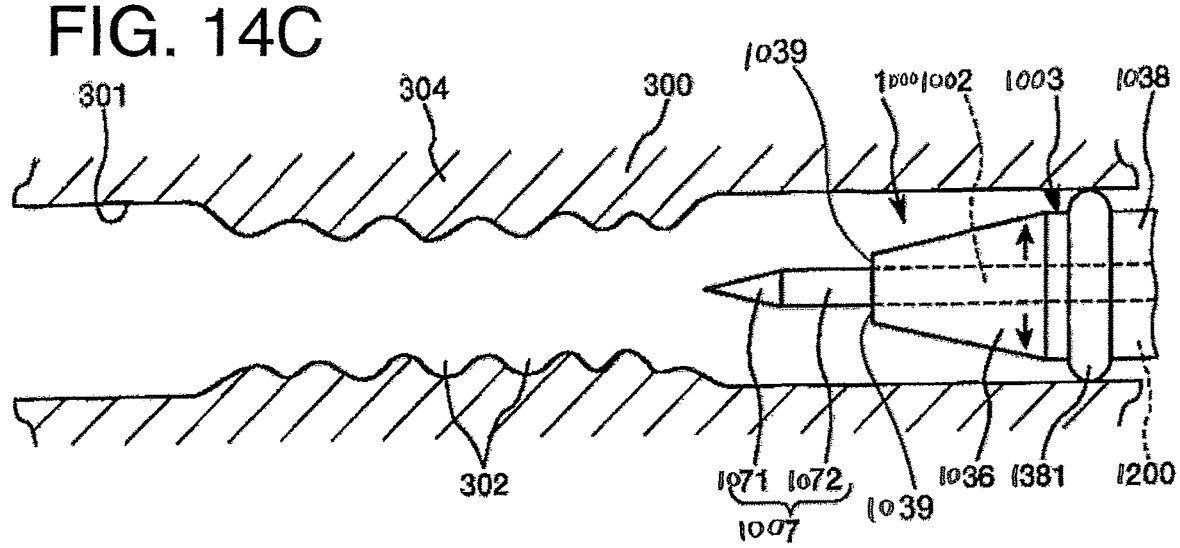
Figure 15A:
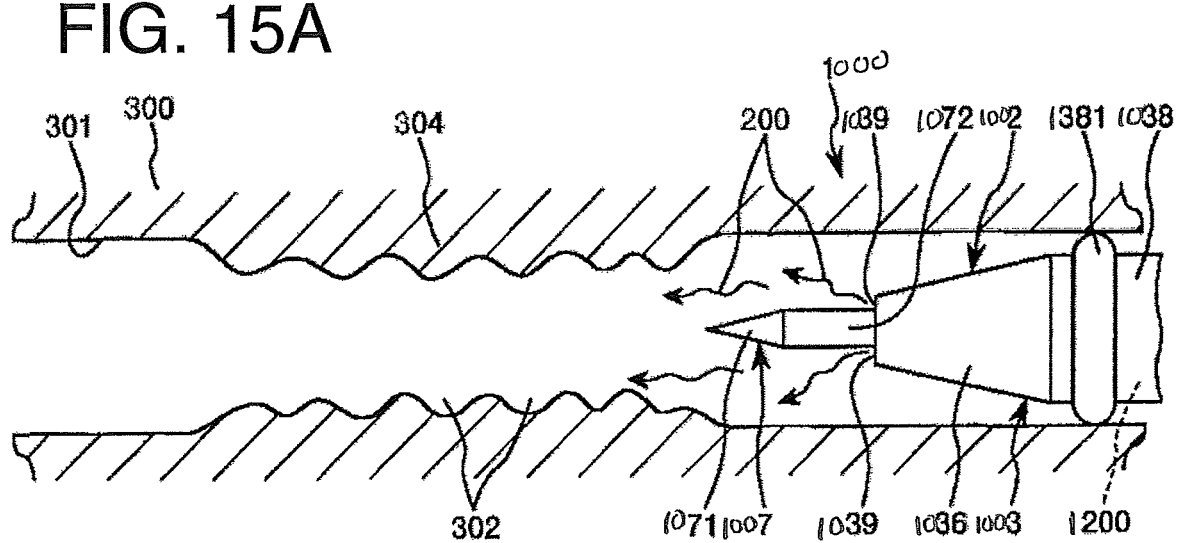
Figure 15B:
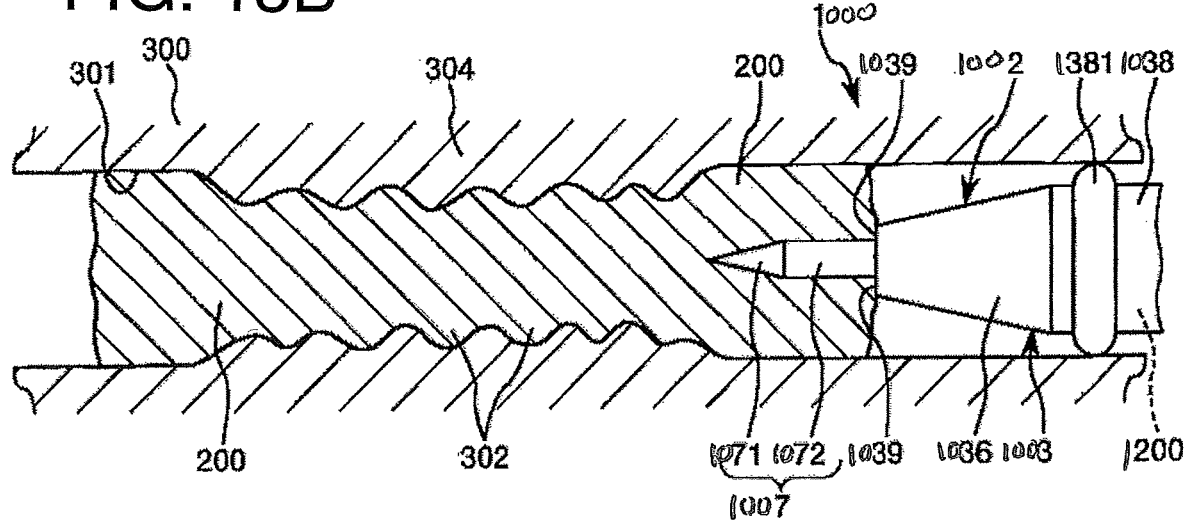
FIG. 15B illustrates a state in which filling with the gel has been completed.
Figure 15C:
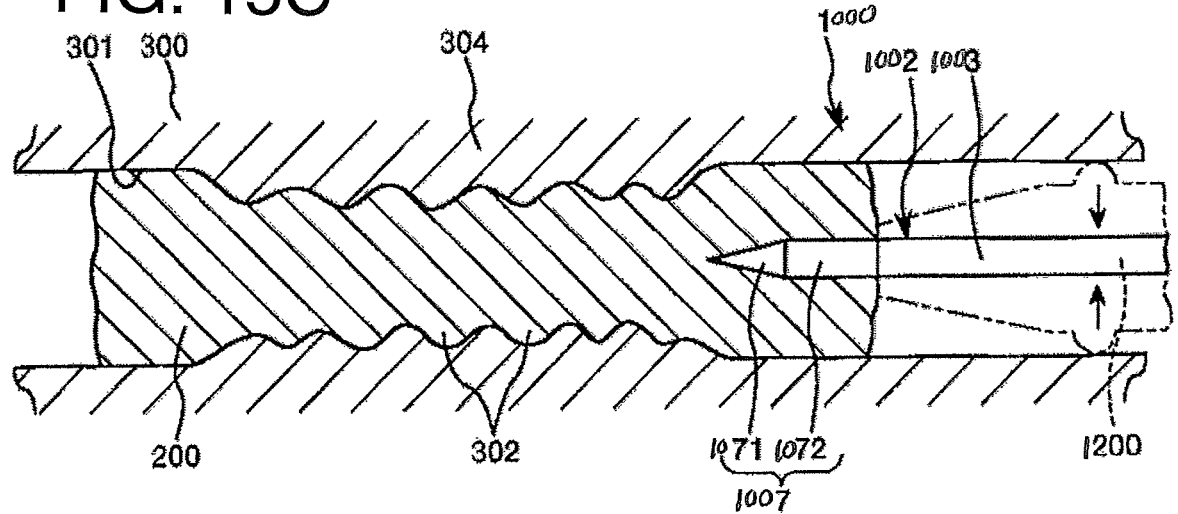
FIG. 15C illustrates a state in which the balloon unit is contracted.
Figure 16A:
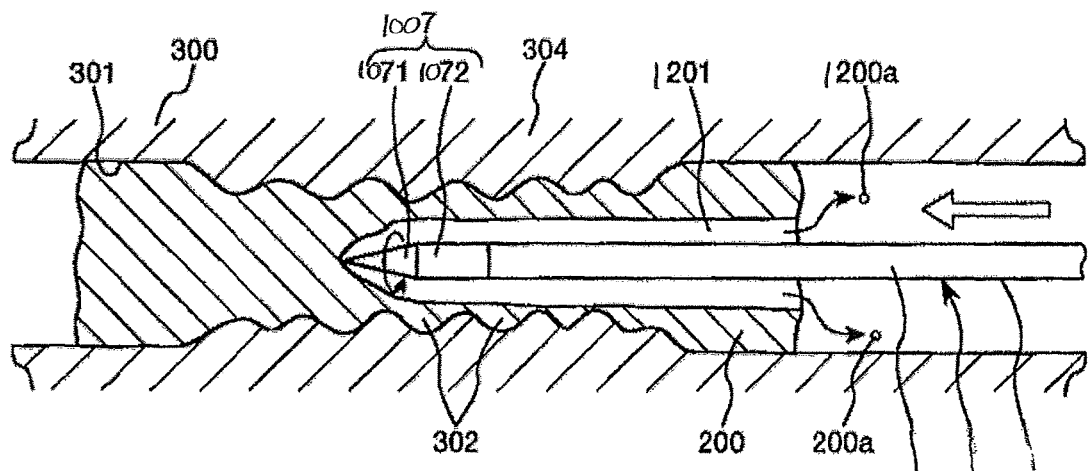
Figure 16B:
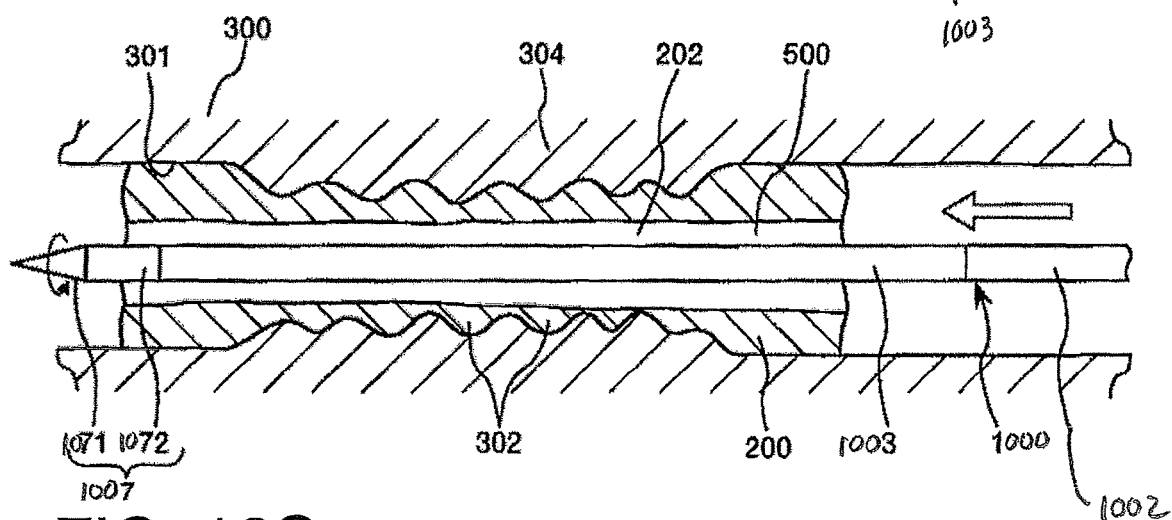
Figure 16C:
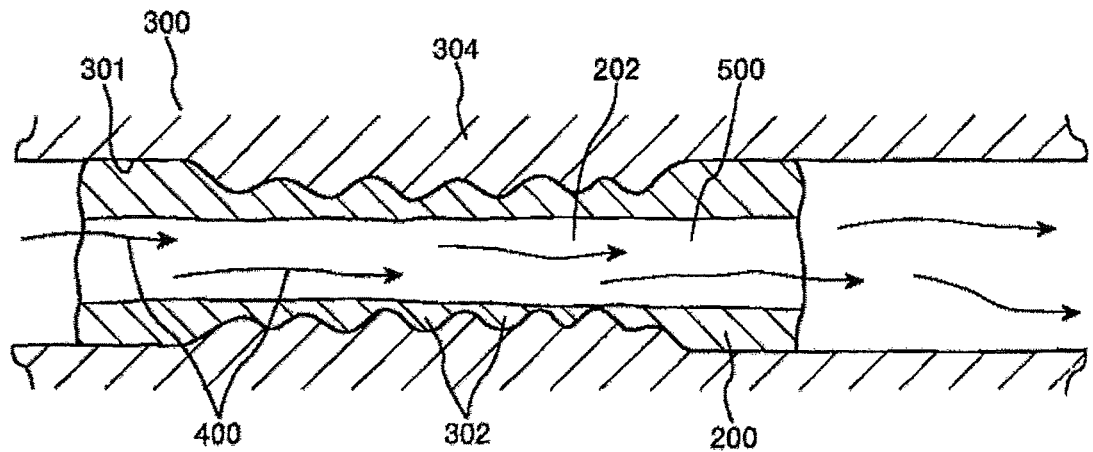

FIG. 13 is a partial cross-sectional longitudinal view illustrating a sixth embodiment of the medical elongated body according to the present disclosure. FIGS. 14A to 14C are cross-sectional views illustrating the inside of a blood vessel formed with a rugged, projected and recessed pattern, for explaining the sixth embodiment of the blood vessel lumen forming method according to the present disclosure, wherein FIG. 14A illustrates a state before the medical elongated body is inserted into the blood vessel, FIG. 14B illustrates a state in which the medical elongated body is inserted in the blood vessel, and FIG. 14C illustrates a state in which a balloon unit is expanded. FIGS. 15A to 15C are cross-sectional views illustrating the inside of the blood vessel formed with the rugged pattern, for explaining the sixth embodiment of the blood vessel lumen forming method according to the present disclosure, wherein FIG. 15A illustrates a state in which a gel is jetted from a jet section, FIG. 15B illustrates a state in which filling with the gel has been completed, and FIG. 15C illustrates a state in which the balloon unit is contracted. FIGS. 16A to 16C are cross-sectional views illustrating the inside of the blood vessel formed with the rugged pattern, for explaining the sixth embodiment of the blood vessel lumen forming method according to the present disclosure, wherein FIG. 16A illustrates a state in which the gel is being drilled, FIG. 16B illustrates a state in which the drilling of the gel has been completed, and FIG. 16C illustrates a state in which the medical elongated body has been withdrawn out of the blood vessel.

In the following description, for convenience of description, the right side in FIGS. 13 to 16C (and also in FIGS. 17A to 23C) will be referred to as "proximal," and the left side as "distal." In addition, for easy understanding, in FIGS. 13 to 16C (and also in FIGS. 17A to 23C), the dimensions in the longitudinal direction of the medical elongated body are scaled down, while the dimensions in the radial direction are scaled up. Therefore, the dimensions of the medical elongated body, particularly of the balloon unit, in the drawings may be quite different from the actual ones.

As illustrated in FIG. 13, a medical elongated body 1000 includes a flexible catheter body 1002, a balloon unit 1003 configured to be expandable and contractable, and a drill 1007 as a drilling unit.

The catheter body 1002 is an elongated body configured as a flexible tube. The catheter body 1002 has a lumen 1020. The lumen 1020 functions as a passage through which to supply a working fluid to the balloon unit 10003.

In addition, the catheter body 1002 is provided at its distal end portion with a through-hole 1220 which penetrates the catheter body 1002 in its film thickness direction. That is the through-hole 1220 passes through the side wall of the catheter body 1002. The through-hole 1220 functions as a supply section or supply port through which to supply the working fluid into the balloon unit 1003.

At a proximal end portion of the catheter body 1002, there is provided a hub which has a port for supplying the working fluid into the lumen 1020. In this embodiment, the catheter body 1002 is occluded at its distal end.

Examples of the material constituting the catheter body 1002 include various thermoplastic resins or thermosetting resins, such as polyolefin resins, polyamide resins, urethane resins, and polyimide resins. Specific examples include polyolefins such as polyethylene, polypropylene, ethylene-propylene copolymers, ethylene-vinyl acetate copolymers, polyvinyl chloride, polyesters such as polyethylene terephthalate, polybutylene terephthalate, polyurethane, polyamides, polyimides, polystyrene resins, fluororesins, and various thermoplastic elastomers based on styrene, polyolefin, polyvinyl chloride, polyurethane, polyester, polyamide, polybutadiene, fluoro-rubber or the like. Besides, the catheter body 2 may have a multilayer laminate structure formed from a plurality of materials.

In addition, in this embodiment, a gel 200 is used as the working fluid. The gel 200 is preferably constituted of a bio-compatible material. Examples of the applicable bio-compatible material include polyurethane, polyethylene glycol, 2-methacryroyloxyethyl phosphorylcholine (MPC) polymers having a phospholipid polar group, collagen, agarose, hyaluronic acid, chitin, chitosan, acrylic polymers, epoxy polymers, and methacrylic polymers and copolymers, such as poly(2-hydroxy methacrylate).

The gel 200 may be admixed with a drug such as an antithrombogenic agent.

The viscosity of the gel 200 is preferably not less than 1 Pa·s and not more than 150 Pa·s. This helps ensure that after hollows or recesses 302 are filled up with the gel 200, the gel 200 can be prevented from being washed away by blood, as will be described later (see FIG. 16C).

As illustrated in FIG. 13, the balloon unit 1003 is composed of a flexible film member. Both end portions of the balloon unit 1003 are joined, at spaced-apart locations, to a distal end portion of the catheter body 1002 by, for example, heat fusing or the like.

The balloon unit 1003 is expanded by supplying the gel 200 into the balloon unit through the lumen 1020. Then, the balloon unit 1003 is contracted or reduced in size, from the expanded state to a contracted state, by drawing out the gel 200 from the balloon unit.

In addition, the balloon unit 1003 includes a tapered section 1036 located at a distal end portion of the balloon unit 1003, a tapered section 1037 located at a proximal end portion of the balloon unit 1003, and an intermediate section 1038 located between the tapered section 1036 and the tapered section 1037.

The tapered section 1036 in its expanded state is shaped such that its outside diameter gradually decreases in the distal direction. The tapered section 1037 in its expanded state is shaped such that its outside diameter gradually decreases in the proximal direction.

The intermediate section 1038 is a portion which makes contact with the blood vessel wall when expanded. In addition, the intermediate section 1038 has two annular projected portions 1381 at positions shifted from each other in the longitudinal direction thereof. This helps ensure that in a state in which the intermediate section 1038 is in contact with the blood vessel wall, the blood vessel can be occluded reliably.

At a distal end of the tapered section 1036, or at a distal end of the balloon unit 1003, there are provided a plurality of jet ports 1039 composed of through-holes which penetrate the distal end in the film thickness direction of the distal end. That is the jet ports 1039 pass through the wall of the balloon unit 1003. The jet ports 1039 functions as jet sections through which the gel 200 in the balloon unit 1003 is jetted out toward the distal side of the balloon unit 1003.

Since the gel 200 has the viscosity as above-mentioned, the gel 200 is prevented from being jetted out through the jet ports 1039 before the balloon unit 1003 is brought into the expanded state and the pressure inside the balloon unit 1003 exceeds a predetermined value.

The material constituting the balloon unit 1003 is not particularly limited. Examples of the constituent material include polyester resins or polyester elastomers such as polyethylene terephthalate, polybutylene terephthalate, olefin resins such as polyethylene, polypropylene, which may or may not be cross-linked by irradiation with electron rays, polyvinyl chloride resins, polyamide resins or polyamide elastomers such as nylon 11, nylon 12, nylon 610, etc., polyurethane resins, ethylene-vinyl acetate copolymer, which may or may not be cross-linked by irradiation with electron rays, and polymer blends, polymer alloys and the like containing at least one of these resins.

As illustrated in FIG. 13, the drill 1007 is a rotating body configured to be rotatable about a center axis of the medical elongated body 1000. The drill 1007 includes a tapered section 1071 at a distal end portion of the drill, and a constant-outside-diameter section 1072 located on the proximal side of the tapered section 1071. The tapered section 1071 has an outside diameter which gradually decreases in the distal direction. A proximal end portion of the constant-outside-diameter section 1072 is rotatably provided at the distal end of the catheter body 1002.

The method for rotating the drill 1007 is not specifically restricted. Examples of the rotating method include a method in which a shaft is inserted in and passed through the lumen 1020 of the catheter body 1002, the drill 1007 is connected to the shaft and the shaft is rotated, and a method in which the drill 1007 itself incorporates therein a rotational drive source. In addition, in the case where such a shaft is used, the shaft may be manually rotated by the user of the medical elongated body 1000, or may be rotated by connecting the shaft to a rotational drive source.

As the material constituting the drill 1007, there can be used metallic materials, rigid resin materials and the like, metallic materials are preferable. This helps ensure that the drill 1007 can be prevented from being damaged, even upon making contact with, for example, a thrombus or a calcified part.

Examples of the metallic materials include various metals such as iron, nickel, stainless steel, copper, brass, aluminum, titanium, and alloys containing these metals.

Examples of the rigid resin materials include polyolefins such as polyethylene, polypropylene, ethylene-propylene copolymers, polyvinyl chloride, polystyrene, polyamides, polyimides, polycarbonate, poly(4-methylpentene-1), ionomers, acrylic resins, polymethyl methacrylate, acrylonitrile-butadiene-styrene copolymers, acrylonitrile-styrene copolymers, butadiene-styrene copolymers, polyesters such as polyethylene terephthalate, polybutylene terephthalate, polyethers, polyether ketones, polyether ether ketones, polyether imides, polyacetal, polyphenylene oxide, polysulfone, polyether sulfones, polyphenylene sulfide, polyallylate, aromatic polyesters, polytetrafluoroethylene, polyvinylidene fluoride, other fluororesins, epoxy resins, phenolic resins, urea resins, melamine resins, silicone resins, polyurethane, and copolymers, polymer blends, polymer alloys and the like containing these polymers as main constituents. These rigid resin materials may be used either singly or in combination of two or more of them.

In the case where such a resin material is used, it is preferable that the drill 1007 is provided with abrasive grains at a surface thereof.

Now, a method of using the medical elongated body 1000 described above, or the blood vessel lumen forming method according to the present disclosure will be described below, referring to FIGS. 14A to 16C.

The blood vessel lumen forming method according to the present disclosure includes [1] an insertion step, [2] a partitioning step, [3] a filling step, [4] a drilling step, and [5] a withdrawing step.

First, a blood vessel 300 into which the medical elongated body 1000 is to be inserted will be described.

The blood vessel lumen forming method according to the present disclosure is used for a treatment of peripheral vascular site. In the following description, there is an explanation of a method of inserting the medical elongated body 1 into the blood vessel from under the knee in order to treat peripheral vascular site.

As illustrated in FIG. 14A, a blood vessel wall 301 of the blood vessel 300 has a rugged, projected and recessed pattern 304 due to bulging of the blood vessel wall 301 to the inside (radially inward) of the blood vessel 300. Such a rugged pattern 304 is formed due to, for example, Monckeberg type medial calcification in which a middle coat of the blood vessel 300 is thickened through calcification.

In this case, the flow of blood 400 is disturbed at the rugged pattern 304, and, particularly, the blood 400 stagnates in hollows or recesses 302 of the rugged pattern 304. The blood stagnation or turbulence causes thrombus formation, and, depending on the extent of the thrombus formation, the blood vessel 300 may be occluded.

In FIGS. 14A to 16C, the left side is the upstream side with respect to the blood flow, and the right side is the downstream side. Accordingly, in the blood vessel 300, the blood 400 flows from the left side toward the right side in FIGS. 14A to 16C.

[1] Insertion Step

As depicted in FIG. 14B, the medical elongated body 1000 is inserted into the blood vessel 300. In this instance, the medical elongated body 1000 is inserted until the jet ports 1039 of the medical elongated body 1000 are located in the downstream-side vicinity of the rugged pattern 304. For example, a contrast marker which is radiopaque is provided in the vicinity of the jet ports 1039 of the medical elongated body 1000, and the inserting operation is conducted under radioscopy, whereby positioning of the jet ports 1039 can be easily performed.

In this insertion step, the balloon unit 1003 is in a contracted state.

[2] Partitioning Step

Next, as illustrated in FIG. 14C, the gel 200 is supplied into the balloon unit 1003 to expand the balloon unit 1003. As a result, the inside of the blood vessel 300 is partitioned by the balloon unit 1003. Therefore, the blood 400 is dammed up by the balloon unit 1003, whereby a blood flow stop state can be obtained.

[3] Filling Step

Subsequently, the gel 200 is further supplied into the balloon unit 1003. When the pressure inside the balloon unit 1003 exceeds a predetermined value, the gel 200 is jetted out through the jet ports 1039 (see FIG. 15A).

In this instance, since the blood flow stop state is established inside the blood vessel 300, the gel 200 thus jetted can be prevented from being washed away downstream by the blood flow. Therefore, filling with the gel 200 proceeds toward the upstream side (upstream from the expanded balloon unit 1003). In this case, the gel 200 progressively fills up the blood vessel 300 while entering into and filling up the hollows or recesses 302.

Particularly, since the filling with the gel 200 proceeds from the downstream side toward the upstream side, the gel 200 gradually fills up the hollows or recesses 302 while pushing back the blood 400 upstream. Therefore, the hollows or recesses 302 can be thoroughly filled up with the gel 200.

Then, as depicted in FIG. 15B, the inside of the blood vessel 300 is occluded by the gel 200 over the whole range of the rugged pattern 304, or from the upstream side to the downstream side of the rugged pattern 304.

In this embodiment, the range of filling with the gel 200 protrudes to the upstream side and the downstream side of the rugged pattern 304. That is, the gel 200 extends both upstream from and downstream from the rugged pattern 304 nside the blood vessel 300.

Then, after the filling with the gel 200 is completed, the gel 200 (i.e., gel 200 in the balloon unit 300 that has not been expelled into the blood vessel) is drawn through a port provided at a proximal end portion of the catheter body 1002, to contract the balloon unit 1003, as illustrated in FIG. 15C.

[4] Drilling Step

Next, as illustrated in FIG. 16A, while rotating the drill 1007, the medical elongated body 1 is pushed straight forward toward the upstream side. By this, the gel 200 is drilled by the drill 1007, and a lumen 201 is progressively formed where the drill 1007 passes. Since the drill 1007 is being rotated, the inside diameter of the lumen 201 is greater than a maximum outside diameter of the drill 1007.

Debris 100a of the gel 200 drilled by the drill 1007 goes out (i.e., is removed or carried away) via the downstream side of the lumen 201 to the outside of the lumen 201.

Then, with the medical elongated body 1000 pushed further distally, the drill 1007 penetrates the gel 200 (see FIG. 16B). As a result, the lumen 201 depicted in FIG. 16A becomes a through-hole 202. The through-hole 202 functions as a passage 500 through which the blood 400 can flow downstream.

In addition, where the amount of rotation of the drill 1007 is kept constant when the drill 1007 is pushed forward, the inside diameter of the passage 500 can be made substantially constant along the longitudinal direction of the passage 500. Therefore, an inner circumferential surface of the passage 500 can be made smooth.

[5] Withdrawing Step

Then, the medical elongated body 1000 is accommodated into an outer tube, and, in the accommodated state, it is withdrawn out of the blood vessel 300.

According to the blood vessel lumen forming method of the present disclosure as described above, in the filling step, the inside of the blood vessel 300 is filled up with the gel 200 while the gel 200 fills-up the hollows or recesses 302 of the rugged pattern 304 generated in the blood vessel wall 301. Then, the gel 200 (part of the gel 200) made to fill up the blood vessel 300 by the filling step is drilled and thereby removed, to form the passage 500. In addition, by pushing the medical elongated body 1000 straight forward while rotating the drill 1007, the passage 500 with the smooth inner circumferential surface can be obtained.

According to the passage 500 obtained in this manner, stagnation or turbulence of the blood 100 in the vicinity of the hollows 302 as illustrated in FIG. 14A can be prevented from occurring. Therefore, the blood flow in the vicinity of the hollows or recesses 302 can be normalized and smoothened. This makes it possible to inhibit thrombus formation in the vicinity of the hollows 302 and to prevent the blood vessel 300 from being stenosed. As a result, the cross-sectional area of that portion of the blood vessel 300 where the blood 400 passes can be prevented from being reduced excessively. In this embodiment, only the gel 200 is drilled, in other words, the drilling is conducted while avoiding the rugged pattern 304, in the drilling step. By virtue of this, breaking of the drill 1007 due to contact between the rugged pattern 304 and the drill 1007 can be securely prevented.

In addition, the above description has been made while illustrating a rugged pattern arising from medial type calcification as an example. In the present disclosure, however, the smoothening can also be achieved when applied to a rugged pattern due to a thrombus generated at a blood vessel wall, a rugged pattern arising from arterial sclerosis, a rugged pattern due to a plaque which is a macular hypertrophic lesion of an inner membrane present at a focus of artery sclerosis, etc. This is because hollows formed in various sizes and shapes due to bulging of a blood vessel wall to the inside of a blood vessel can be thoroughly filled up with the gel, and a passage with a smooth inner circumferential surface can be formed by drilling the filling gel, in this embodiment. Specifically, in regard of rugged patterns arising from various abnormalities in blood vessels as above-mentioned, it is possible to normalize and smoothen the blood flow in the vicinity of the rugged patterns, regardless of characteristic features of the rugged patterns.

Although coronary arteries and the like can be comparatively easily treated by use of stents, treatment with stents is difficult to achieve in peripheral comparatively thin blood vessels. Specifically, there are cases where it is difficult to pass a stent delivery catheter across a rugged pattern generated in a comparatively thin blood vessel.

On the other hand, in the blood vessel lumen forming method in this embodiment, it is required only to push the medical elongated body 1000 forward up to a position just on the proximal side of that portion of the blood vessel 300 where the rugged pattern 304 is formed. In other words, in the blood vessel lumen forming method in this embodiment, the passage across the rugged pattern 304 can be omitted. That is, the method here does not require that the medical elongated body 1000 be pushed along and perhaps past the rugged pattern 304. For this reason, it is possible to achieve treatment in peripheral comparatively thin blood vessels, which have hitherto been difficult to treat with stents.

The balloon unit 1003 in the medical elongated body 1000 may be omitted, and the blood vessel lumen forming method of the present disclosure can also be conducted using an ordinary medical elongated body. In this case, the medical elongated body has a radially expandable portion omitted, and, therefore, treatment in thinner blood vessels can be performed with such a medical elongated body.

As described above, the blood vessel lumen forming method in the present disclosure is effective for treatment in lower limb region.

Further, generation of a rugged pattern at a blood vessel wall due to medial type calcification is liable to occur in a lower limb region. By preventing thrombus formation from arising from such a rugged pattern, it is possible to stop a cascade of organization, inflammation or intimal thickening.

<Seventh Embodiment>

Figure 17A:
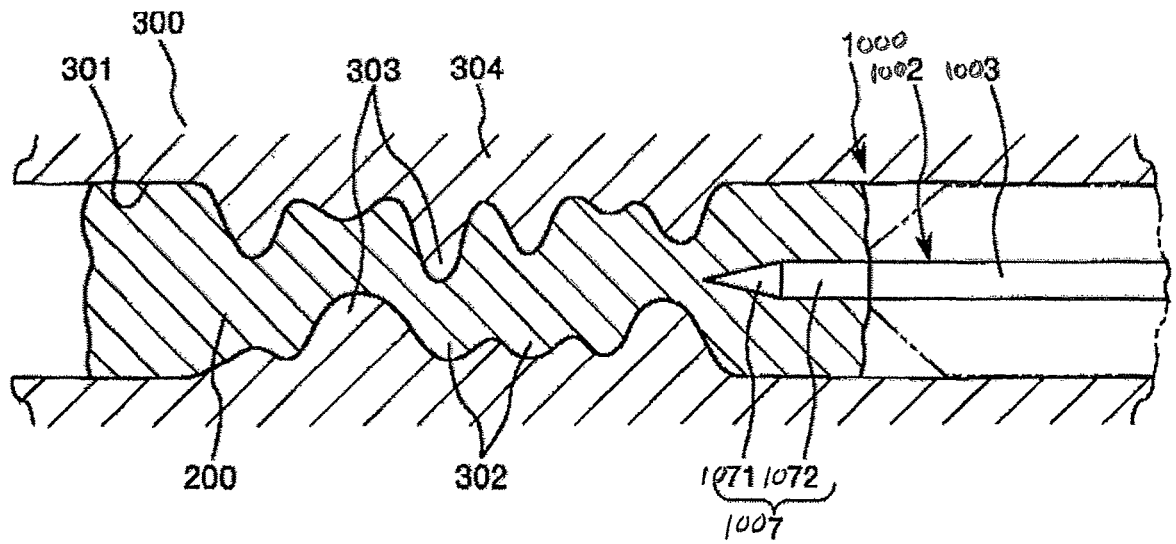
Figure 17B:
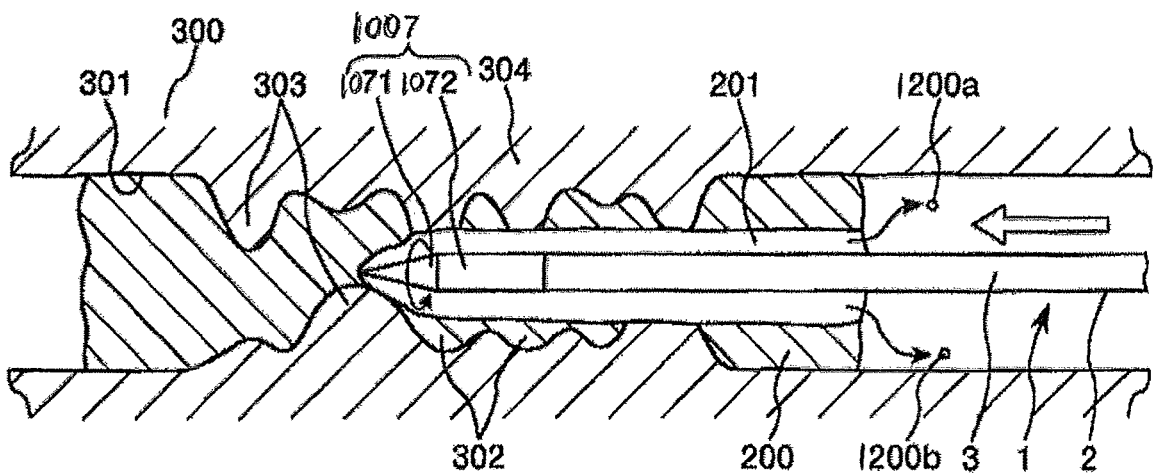
Figure 17C:
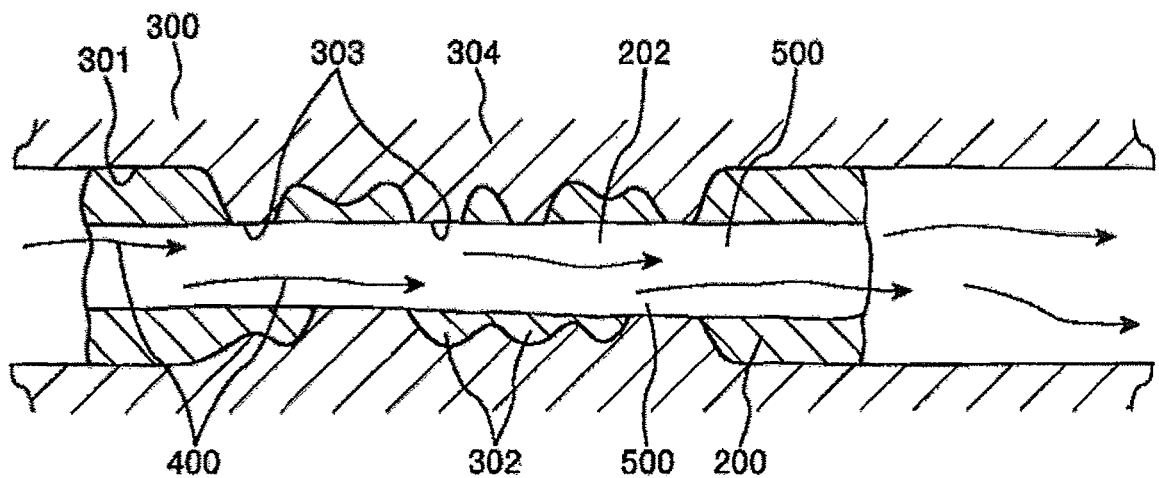

FIGS. 17A to 17C are cross-sectional views illustrating the inside of a blood vessel formed with a rugged pattern, for explaining a second embodiment of the blood vessel lumen forming method according to the present disclosure, wherein FIG. 17A illustrates a state in which filling with a gel has been completed and a balloon unit is contracted, FIG. 17B illustrates a state in which the gel is being drilled together with crests of the rugged pattern, and FIG. 17C illustrates a state in which the medical elongated body has been withdrawn out of the blood vessel.

Referring to these figures, the seventh embodiment of the blood vessel lumen forming method and the medical elongated body according to the present disclosure will be described below. The following description will primarily focus on differences from the sixth embodiment above, and a detailed description of features already described above will not be repeated.

This embodiment is the same as the sixth embodiment above, except for differences mainly in the drilling step.

As illustrated in FIG. 17A, in this embodiment, a case where crests 303 of a rugged pattern 304 generated at a blood vessel wall 301 protrude to the inside, or the side of a center axis of a blood vessel 300, more than in the first embodiment will be described. That is, the method disclosed here has useful application when the rugged pattern 304 is configured so that the crests 303 of the rugged pattern 304 project radially inwardly farther than the center axis of the blood vessel such as shown in FIG. 17. In this embodiment, using a medical elongated body 1000 the same as that in the first embodiment, [1] an insertion step, [2] a partitioning step and [3] a filling step are conducted in the same manner as in the first embodiment, to obtain a state where filling with a gel 200 has been completed (see FIG. 17A).

[4] Drilling Step

Then, as depicted in FIG. 17B, while rotating the drill 1007, the medical elongated body 1000 is pushed straight forward toward the upstream side. In this instance, the gel 100 is drilled together with the crests 303 of the rugged pattern 304. The gel 200 and the crests 303 constituting parts of the rugged pattern 304 are thus removed, and a lumen 201 is progressively formed.

In this case, it is preferable for the medical elongated body 1000 to be pushed forward more slowly than in the first embodiment. By virtue of this, the crests 303 can be drilled reliably, and breaking of the crests 303 in the process of drilling the crests or breakage of the drill 1007 can be prevented from occurring.

Then, the drilling is conducted until the gel 200 is pierced through, and [5] a withdrawing step is conducted in the same manner as in the first embodiment.

According to this embodiment as above, even in a case where the crests 303 of the rugged pattern 304 are protruding to the inside, or even in a case where the state of a disease is comparatively worsened and stenosis of a blood vessel 300 is worsened, a passage 500 with a smooth inner circumferential surface can be formed, and blood flow can be normalized and smoothened.

The medical elongated body 1000 may have a suction section at an arbitrary position of a balloon unit 1003, for example. In this embodiment, as depicted in FIG. 17B, debris 200a of the gel 200 and debris 200b of the crests 303 are generated upon drilling. Particularly, the debris 200b flows downstream through the lumen 201 in the blood vessel 300 as foreign matter. Where the suction section is provided, the foreign matter can be sucked and collected. Besides, the debris 200b may be collected by an outer tube which is not illustrated.

<Eighth Embodiment>

Figure 18:
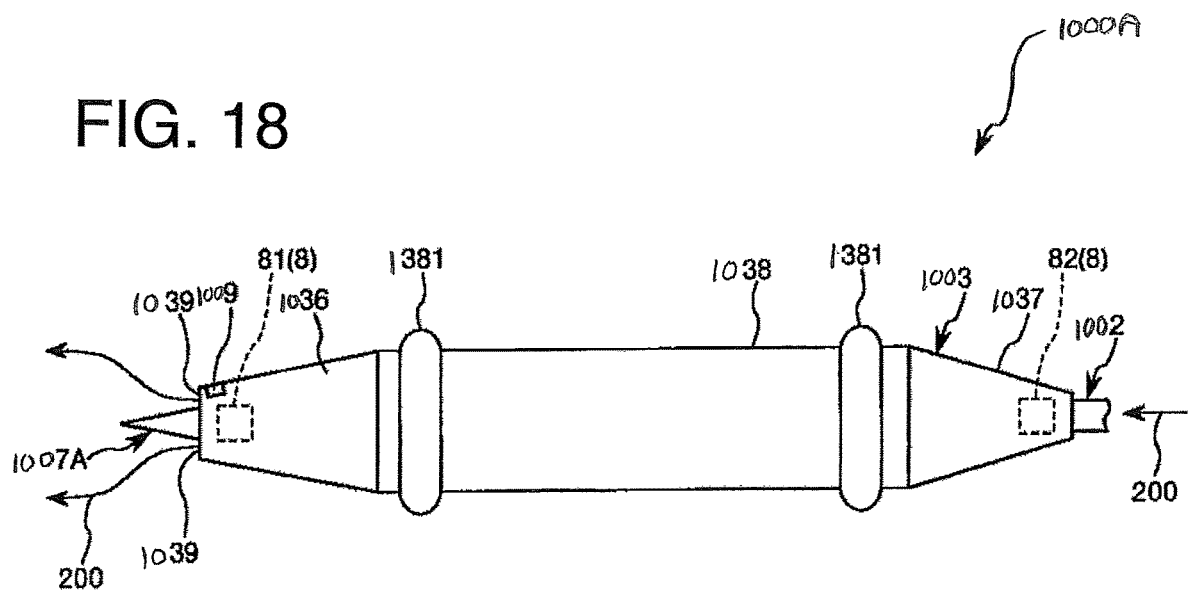
FIG. 18 is a side view of a distal end portion in an eighth embodiment of the medical elongated body according to the present disclosure.
Figure 19:
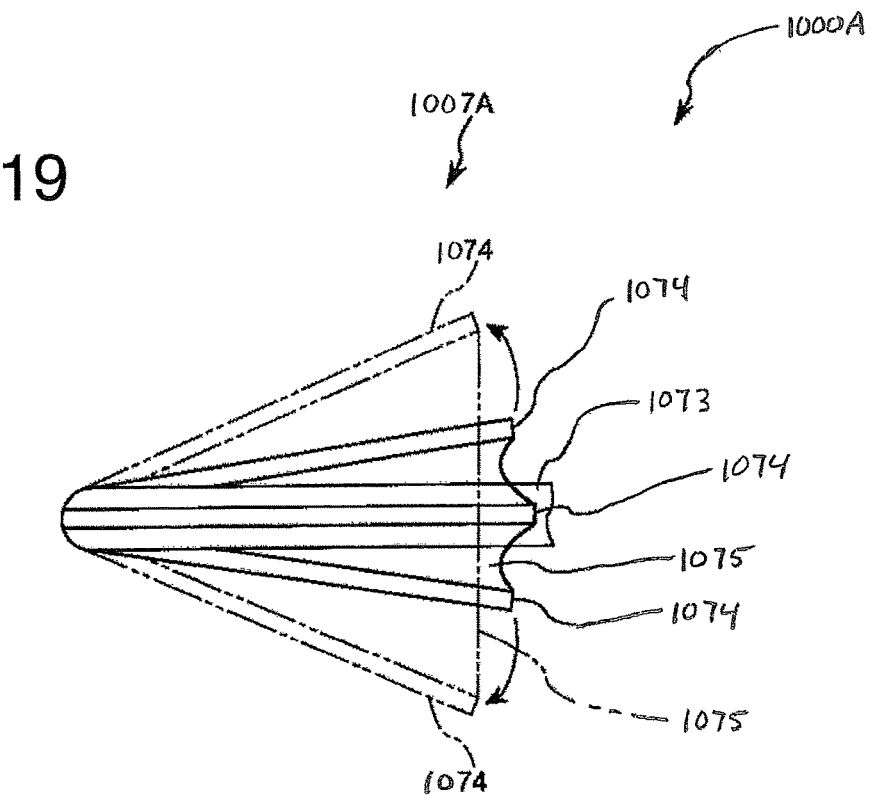
FIG. 19 is an enlarged view of a drilling unit illustrated in FIG. 18.
Figure 20A:
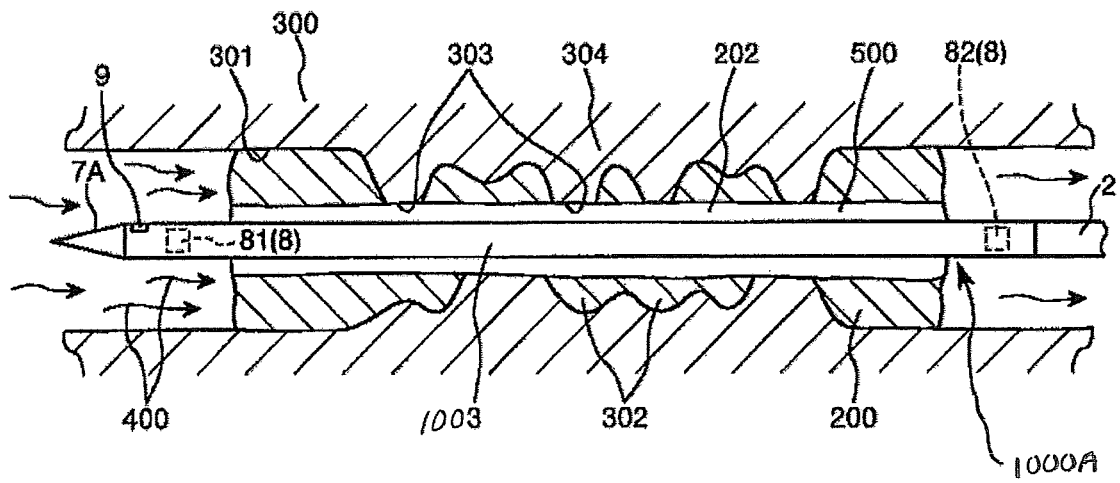
Figure 20B:
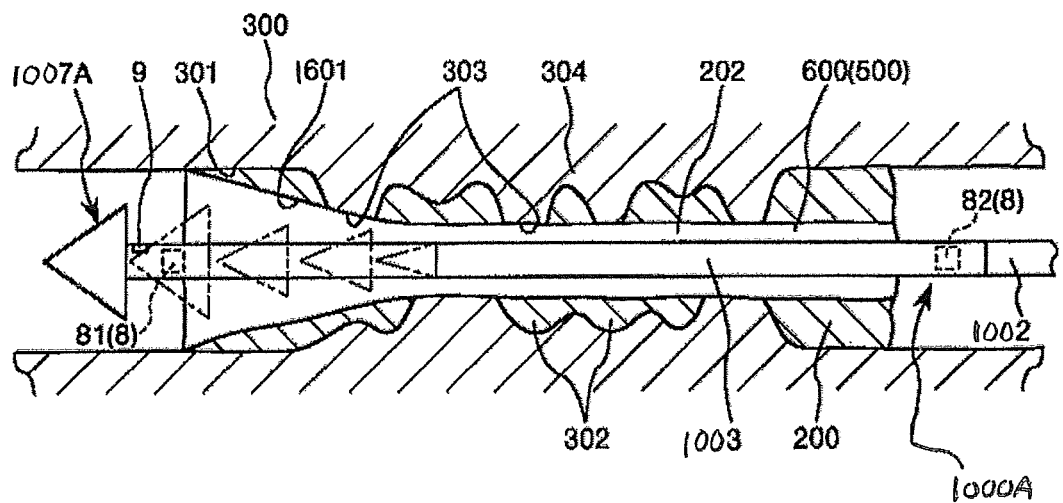
Figure 20C:
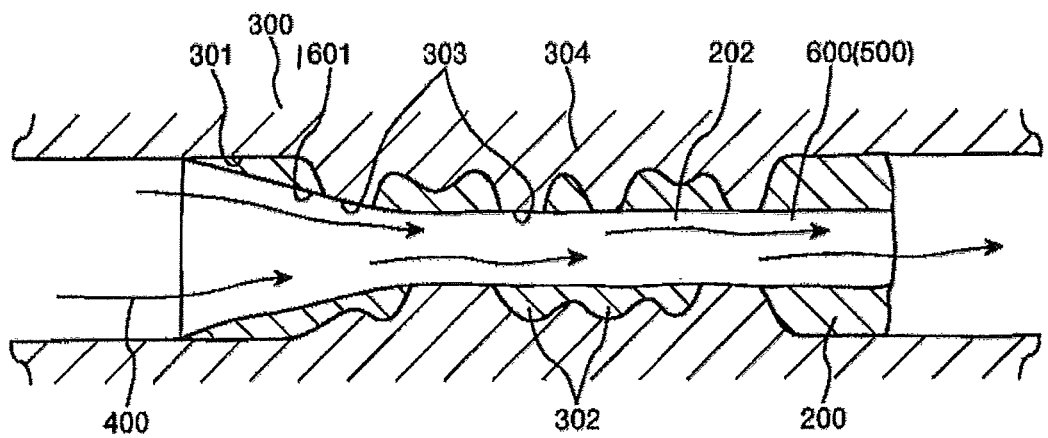

FIG. 18 is a side view of a distal end portion in an eighth embodiment of the medical elongated body according to the present disclosure. FIG. 19 is an enlarged view of a drilling unit illustrated in FIG. 18. FIGS. 20A to 20C are cross-sectional views illustrating the inside of a blood vessel formed with a rugged pattern, for explaining the eighth embodiment of the blood vessel lumen forming method according to the present disclosure, wherein FIG. 20A illustrates a state in which blood pressure is being detected, FIG. 20B illustrates a state in which drilling is under way, and FIG. 20C illustrates a state in which the drilling has been completed.

Referring to these figures, the eighth embodiment of the blood vessel lumen forming method and the medical elongated body according to the present disclosure will be described below. The following description will focus primarily on differences from the above-described embodiments, and a detailed description of features already described above will not be repeated.

This embodiment is the same as the second embodiment above, except for differences mainly in the drilling step.

First, a medical elongated body 1000A will be described.

As illustrated in FIG. 18, the medical elongated body 1000A includes a blood pressure detection unit 8 which is provided at a distal end portion of a catheter body 1002 and adapted to detect blood pressure, and an imaging element 9. The blood pressure detection unit 8 includes a distal-side detection section 81, and a proximal-side detection section 82 disposed on the proximal side with respect to the distal-side detection section 81.

The results of detection by the distal-side detection section 81 and the proximal-side detection section 82 can be displayed on a monitor for example.

In addition, as the distal-side detection section 81 and the proximal-side detection section 82, known blood pressure detection units can be used respectively.

The imaging element 9, in this embodiment, is provided at a distal end portion of a balloon unit 1003. The imaging element 9 is composed of a charge coupled device (CCD) camera, for example. A video or still image picked up by the imaging element 9 is displayed on a monitor, not illustrated, for example.

As depicted in FIG. 19, a drill 1007A of the medical elongated body 1000A is configured to be radially expandable and contractible. The drill 1007A is in the form of an umbrella skeleton including a core member 1073 and a plurality of branch wires 1074 which branch from a distal end portion of the core member 1073. Distal end portions of the branch wires 1074 are supported by a distal end portion of the core member 1073, while proximal end portions of the branch wires 1074 are free ends. In addition, each of the branch wires 1074 can be rotated, or tilted up and down, about the distal end portion of the branch wires 1074.

The branch wires 1074 are covered with a membrane member 1075. This helps ensure that when the branch wires 1074 are turned into a tilted-up state, the membrane member 1075 is also spread, as indicated by alternating long and two short dashes line in FIG. 19. As a result, the drill 1007A is put into a radially enlarged state.

The eighth embodiment of the blood vessel lumen forming method according to the present disclosure will be described below. In this embodiment, after [1] an insertion step, [2] a partitioning step, [3] a filling step and [4] a drilling step (primary drilling step) are conducted in the same manner as in the second embodiment but before [5] a withdrawing step is conducted, [4A] a blood pressure detecting step and [4B] a secondary drilling step are performed. Now, [4A] the blood pressure detecting step and [4B] the secondary drilling step will be described below.

[4A] Blood Pressure Detecting Step

As illustrated in FIG. 20A, the medical elongated body 1000A is again inserted into the passage 500 obtained as a primary passage. Then, the distal-side detection section 81 is exposed to the upstream side beyond the passage 500, and the proximal-side detection section 82 is exposed to the downstream side of the passage 500. In a case where the medical elongated body 1000A is guided into the blood vessel 300 along the direction from the upstream side toward the downstream side with respect to the flow of the blood 400, the distal-side detection section 81 may be exposed to the downstream side of the passage 500 whereas the proximal-side detection section 82 may be exposed to the upstream side of the passage 500.

Next, blood pressure on the upstream side of the passage 500 and blood pressure on the downstream side of the passage 500 are detected by the distal-side detection section 81 and the proximal-side detection section 82. For example in a case where the blood pressure on the upstream side is higher than the blood pressure on the downstream side, the blood is regarded as stagnating. In other words, the inside diameter of the passage 500 is regarded as small.

[4B] Secondary Drilling Step

When the detection of blood pressure has been completed, the medical elongated body 1000A is temporarily retracted toward the proximal side, to position the drill 1007A at an intermediate position of the passage 500. Then, as depicted in FIG. 20B, the drill 1007A is pushed forward in an upstream direction while being rotated. In this case, the rotating speed of the drill 1007A is gradually increased as the drill 1007A is moved toward the upstream side. By virtue of this, as illustrated in FIG. 19, the proximal end portions of the branch wires 1074 are tilted up by centrifugal forces, and the drill 1007A is gradually enlarged in diameter. Therefore, as illustrated in FIG. 20B, the gel 200 and the crests 303 are drilled, and the inside diameter of the passage 500 is progressively enlarged from an intermediate position in the longitudinal direction of the passage 500 toward the upstream side. As a result, the passage 500 illustrated in FIG. 20A is turned into a passage 600, which is a secondary passage, formed with a tapered region 1601 where the inside diameter of the passage 600 increases in the upstream direction as illustrated in FIG. 20B. Thus, in this step, the extent of drilling is increased along the direction toward the upstream side on which the blood pressure is higher.

The passage 600 obtained in this way has such a shape that an inlet of the blood vessel 300 is enlarged, as depicted in FIG. 20C, so that the flow of the blood 400 can be further normalized and smoothened. This result promises the same blood pressure of the rugged pattern 304 in the upstream side and in the downstream side. Therefore, thrombus formation can be prevented more securely. Further, it is possible to confirm that an appropriate blood flow has been secured, thereby immediately confirming a therapeutic effect.

A tapered region where the inside diameter of the passage 500 increases from an intermediate position in the longitudinal direction of the passage 500 toward the downstream side may be formed.

In this embodiment, while imaging an intermediate circumferential surface of the passage 1060 by the imaging element 9, drilling is conducted based on the image obtained. This helps ensure that for example in a case where it is decided, based on the still or video image picked up, that the smoothening of the passage 600 is still insufficient, it is possible to again drill the insufficiently drilled part to thereby smoothen the passage 600.

After the secondary drilling step is completed, [4A] the blood pressure detecting step may be conducted again. Based on the result of this detection, a tertiary drilling step may be performed in the same manner as above.

In addition, while the tapered region 1601 has been formed in the secondary drilling step in this embodiment, the present disclosure is not limited to this configuration. For example, the inside diameter of the passage 500 may be enlarged over the whole range in the longitudinal direction of the passage 500, thereby forming a constant-inside-diameter region.

One of the distal-side detection section 81 and the proximal-side detection section 82 may be omitted. In this case, it is preferable to move one detection section toward the upstream side and toward the downstream side of the passage 500, and to detect blood pressure once at each side to which the detection section is moved.

In addition, while the imaging element 9 is provided at the distal end portion of the balloon unit 1003 in this embodiment, the present disclosure is not limited to this configuration. For example, the imaging element 9 may be provided, for example, at a proximal end portion of the balloon unit 1003 or in the catheter body 1002. Further, a plurality of imaging elements 9 may be provided.

<Ninth Embodiment>

Figure 21:
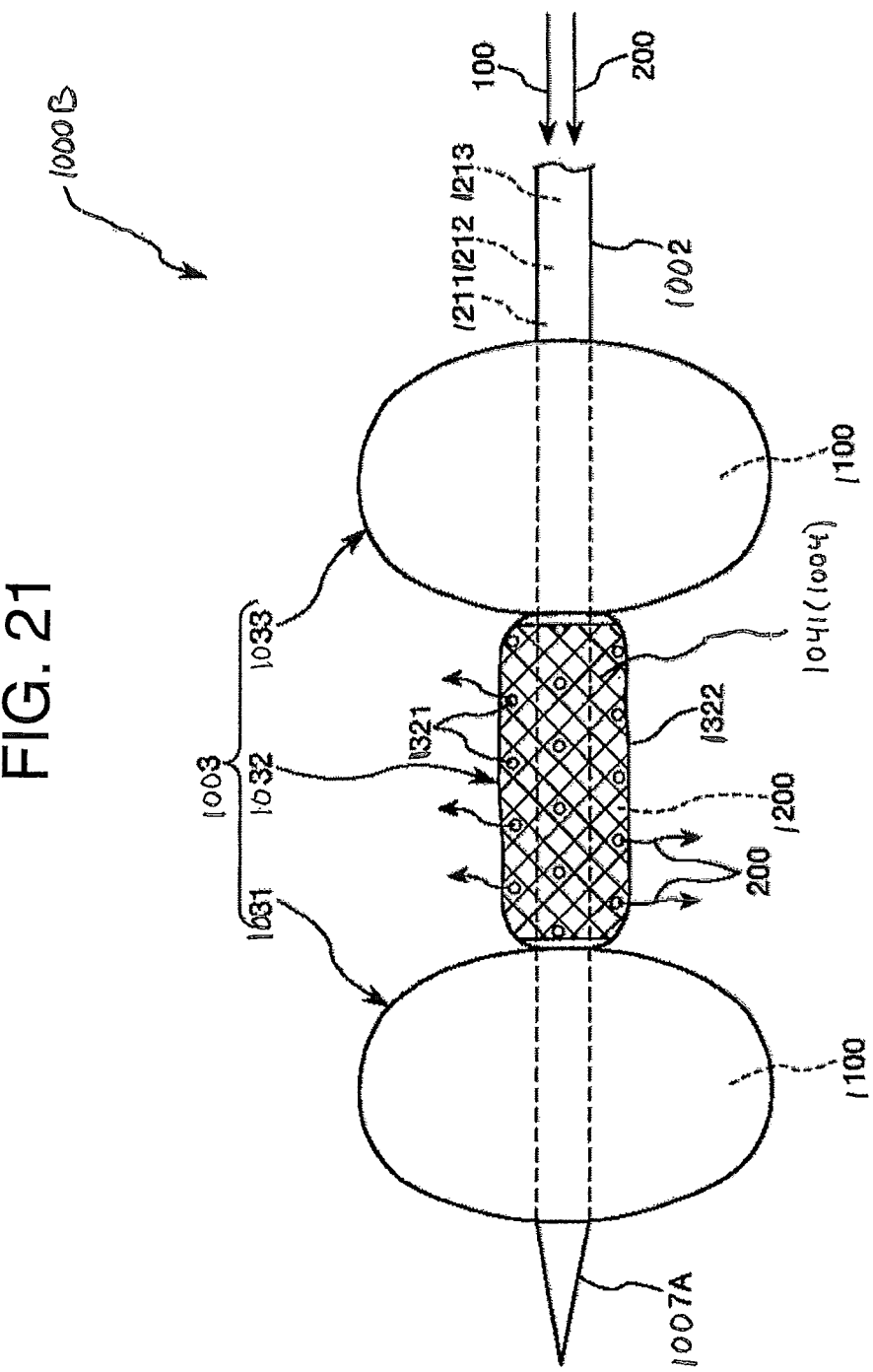
FIG. 21 is a side view of a distal end portion in a ninth embodiment of the medical elongated body according to the present disclosure.
Figure 22A:
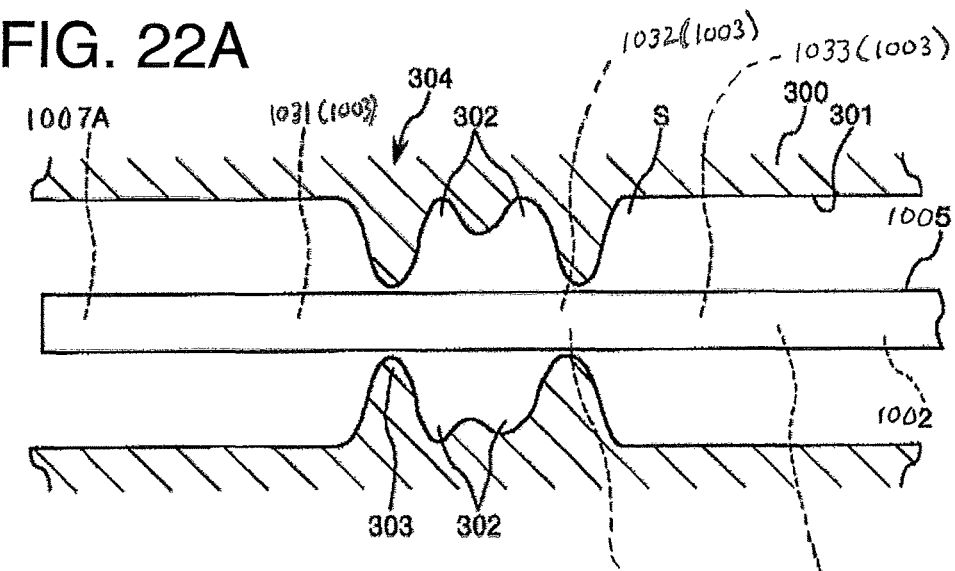
Figure 22B:
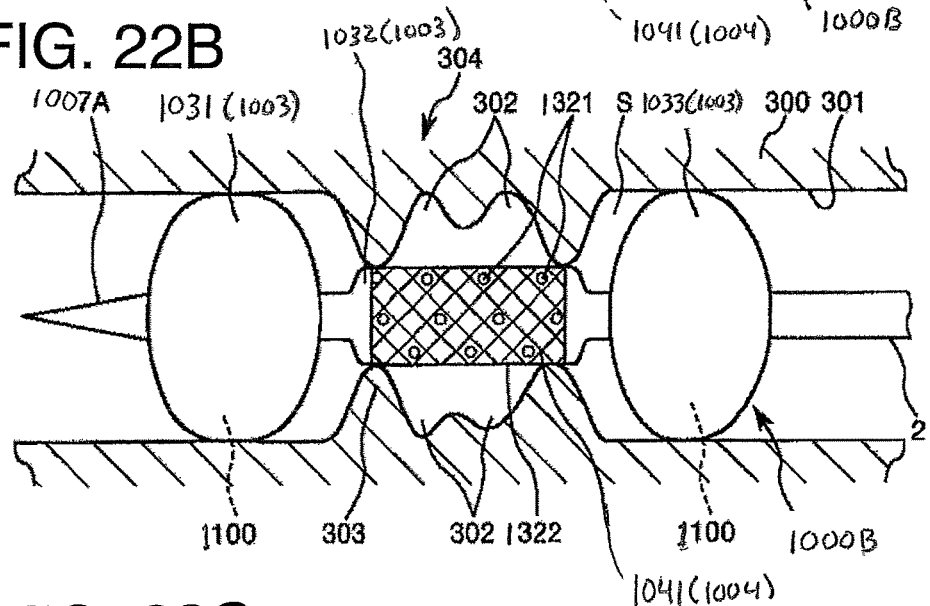
Figure 22C:
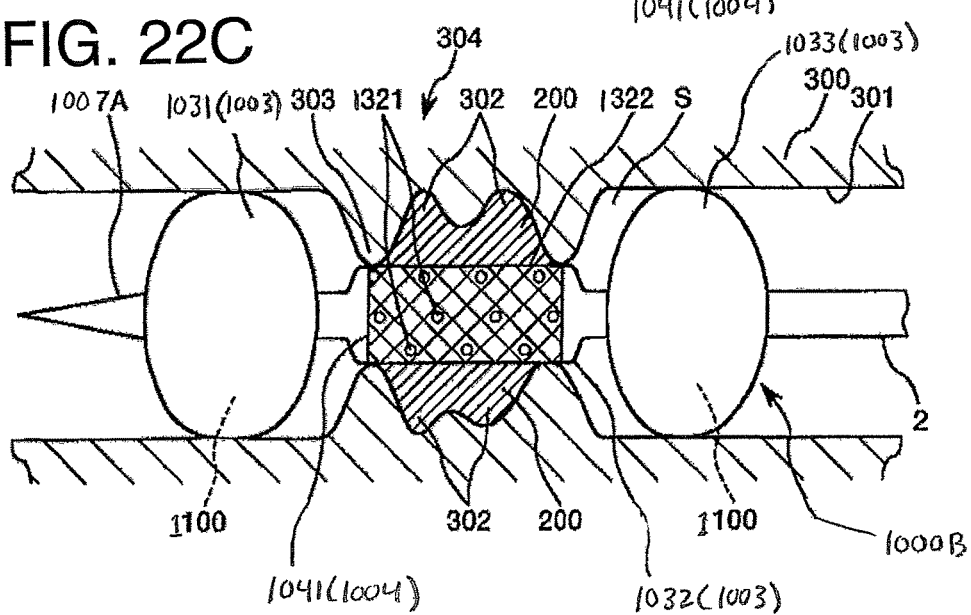
Figure 23A:
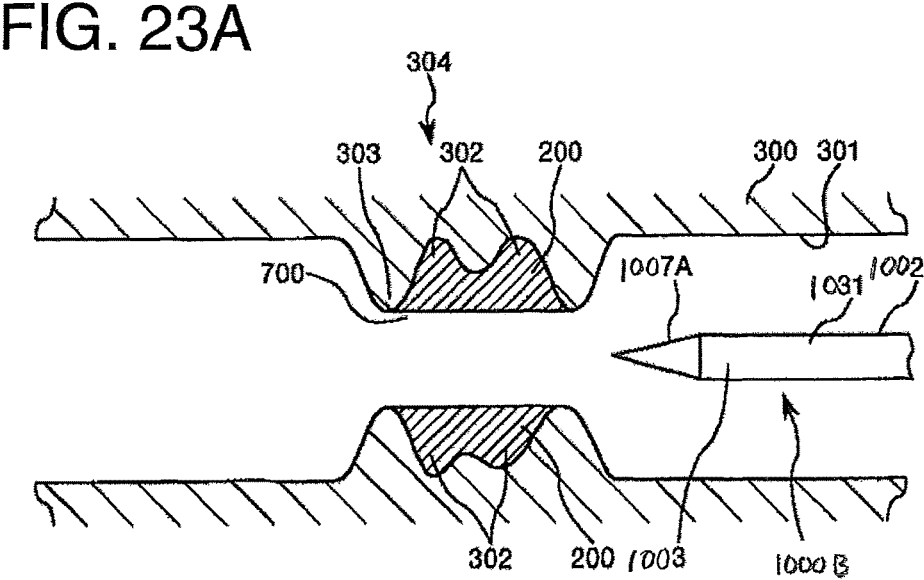
Figure 23B:
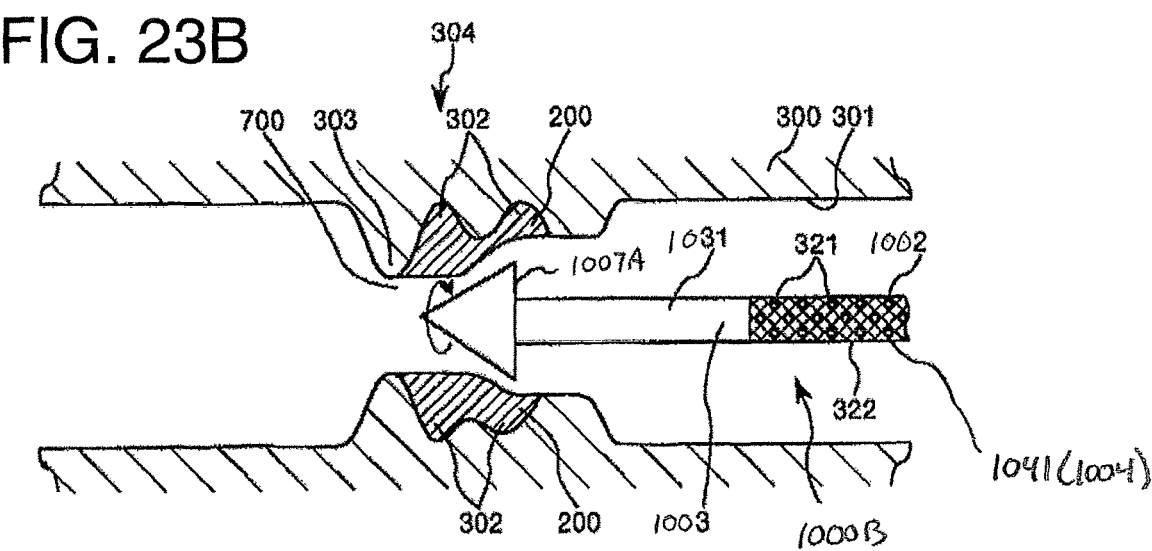
Figure 23C:
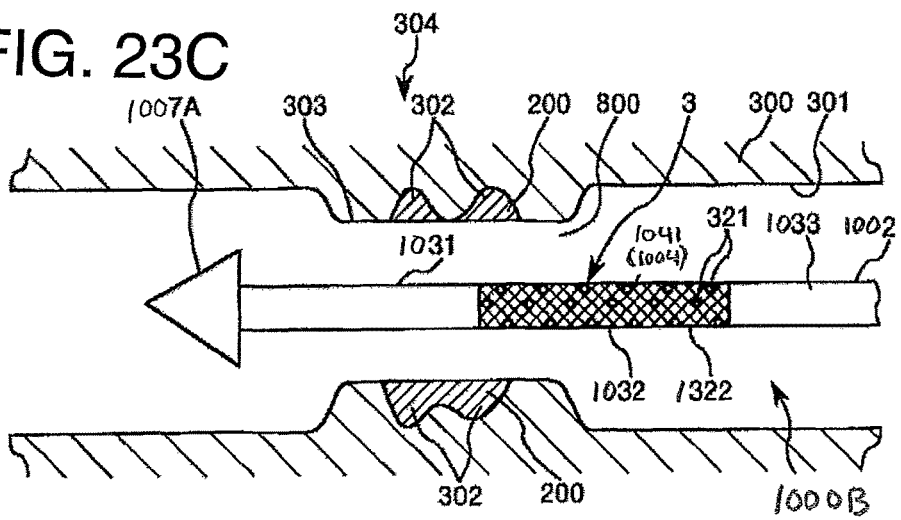

FIG. 21 is a side view of a distal end portion in a ninth embodiment of the medical elongated body according to the present disclosure. FIGS. 22A to 22C are cross-sectional views illustrating the inside of a blood vessel formed with a rugged pattern, for explaining the ninth embodiment of the blood vessel lumen forming method according to the present disclosure, wherein FIG. 22A illustrates a state in which the medical elongated body is inserted in the blood vessel, FIG. 22B illustrates a state in which a balloon unit is expanded, and FIG. 22C illustrates a state in which hollows are filled up with a gel. FIGS. 23A to 23C are cross-sectional views illustrating the inside of the blood vessel formed with the rugged pattern, for explaining the ninth embodiment of the blood vessel lumen forming method according to the present disclosure, wherein FIG. 23A illustrates a state in which the medical elongated body has temporarily been retracted to a proximal side, FIG. 23B illustrates a state in which drilling is under way, and FIG. 23C illustrates a state in which the drilling has been completed.

Referring to these figures, the ninth embodiment of the blood vessel lumen forming method and the medical elongated body according to the present disclosure will be described below. The following description will primarily focus on differences from the above-described embodiments, and a detailed description of features already described above will not be repeated.

This embodiment is the same as the sixth embodiment above, except for differences in the configuration of the balloon unit and in the filling step.

First, a medical elongated body 1000B will be described.

As illustrated in FIG. 21, in the medical elongated body 1000B, a catheter body 1002 has mutually independent lumens 1211, 1212, and 1213. In this embodiment, the drill 1007A as described in the eighth embodiment above is provided at a distal end of the catheter body 1002.

In the medical elongated body 1000B, a balloon unit 1003 includes a distal-side balloon 1031, a jet balloon 1032, and a proximal-side balloon 1033. The distal-side balloon 1031, the jet balloon 1032 and the proximal-side balloon 1033 are arranged in this order from the distal side.

The distal-side balloon 1031 communicates with the lumen 1211, and is expanded by supplying a contrast medium 1100 as a working fluid to the lumen 1211 through the lumen 1211. Then, the distal-side balloon 1031 is contracted by drawing out the contrast medium 100 from the distal-side balloon 1031 by way of the lumen 1211.

The jet balloon 1032 communicates with the lumen 1212, and is expanded by supplying a gel 200 as a working fluid into the jet balloon 1032 through the lumen 1212. Then, the jet balloon 1032 is contracted by drawing out the gel 200 from the jet balloon 1032 through the lumen 1212.

In addition, the jet balloon 1032 has a plurality of jet ports 321 which penetrate the jet balloon 1032 in its film thickness direction (i.e., the jet ports 321 pass through the wall of the jet balloon 1032). When the gel 200 is supplied into the jet balloon 1032 and the pressure inside the jet balloon 1032 exceeds a predetermined value, the gel 1032 is jetted out through the jet ports 1321.

The proximal-side balloon 1033 communicates with the lumen 1213, and is expanded by supplying the contrast medium 1100 as a working fluid into the proximal-side balloon 1033 through the lumen 1213. Then, the proximal-side balloon 1033 is contracted by drawing out the contrast medium 1100 from the proximal-side balloon 1033 through the lumen 1213.

A restricting section 1004 is provided at a jet port formed portion 1322, or that portion of the jet balloon 1032 where the jet ports 1321 are formed. The restricting section 1004 is composed of a net-like body 1041.

The net-like body (net body) 1041 is configured to be radially expandable and contractible. In addition, the net-like body 1041 has a self-expanding property, whereby it is expanded from a contracted state when a restriction on the net-like body 1041 is released. In the expanded state, the net-like body 1041 is hollow cylindrical in shape.

Now, the ninth embodiment of the blood vessel lumen forming method according to the present disclosure will be described.

[1] Insertion Step

As depicted in FIG. 22A, the medical elongated body 10006 in the state of being inserted in (positioned inside) an outer tube 1005 is inserted into a blood vessel 300. In this instance, a state is established in which the distal-side balloon 1031 is located on an upstream side of a rugged pattern 304, whereas the proximal-side balloon 1033 is located on a downstream side of the rugged pattern 304.

[2] Partitioning Step

As illustrated in FIG. 22B, the outer tube 1005 is drawn toward the proximal side or proximal direction, and the distal-side balloon 1031 and the proximal-side balloon 1033 are expanded. As a result, the upstream side and the downstream side of the rugged pattern 304 are partitioned, and a space S in which blood flow at the rugged pattern 304 is stopped is formed.

In addition, since the contrast medium 1100 is used as the working fluid for the distal-side balloon 1031 and the proximal-side balloon 1033, it is possible, by performing the partitioning step under radioscopy, for the operator to reliably grasp the condition that the distal-side balloon 1031 and the proximal-side balloon 33 are expanded and a partition state is established.

As illustrated in FIG. 226, in the partitioning step, the jet balloon 1032 is put into an expanded state by the expansion of the net-like body 1041. In this case, the jet balloon 1032 is expanded while being kept in a substantially cylindrical shape according to the shape of the net-like body 1041. In the expanded state, the jet balloon 1032 or the net-like body 1041 is in contact with crests 303 of the rugged pattern 304, and is restrained from further expansion.

[3] Filling Step

Next, the gel 200 is supplied into the jet balloon 1032, and, when the pressure inside the jet balloon 1032 exceeds a predetermined value, the gel 200 is jetted out through the jet ports 1321. As a result, hollows 302 are filled up with the gel 1100 (see FIG. 22C).

Here, in a case where the net-like body 1041 is omitted, or where the limit of expansion of the jet balloon 1032 is not restricted, the soft and flexible jet balloon 1032 would in its expanded state enter into the hollows or recesses 302 in such a manner that its outside diameter conforms to the rugged pattern 304. In this entered state, it is difficult to jet the gel 200 into the hollows or recesses 302 to fill up the hollows or recesses 302 with the gel 200.

On the other hand, in the medical elongated body 10008 disclosed by way of example here, the limit of expansion of the jet balloon 1032 is restricted by the net-like body 1041. In the expanded state, therefore, a gap is formed between the jet port formed portion 1322 (outer surface of the jet port formed portion 1322) and the inner surfaces of the hollows 302. Accordingly, by jetting the gel 200 into the gap, it is possible to fill up the hollows or recesses 302 with the gel 200.

Subsequently, as illustrated in FIG. 23A, the balloon unit 1003 is contracted or deflated, and the medical elongated body 10008 is temporarily retracted to the proximal side. As a result, in the blood vessel 300, a passage 700 as a small-diameter passage is formed in a part where the medical elongated body 1000B has been located.

Then, a state is established in which the drill 1007A is located on the downstream side of the rugged pattern 304.

[4] Drilling Step

Then, as depicted in FIG. 23B, the drill 1007A is rotated and thereby put into a radially enlarged state, and the medical elongated body 1000B is pushed forward toward the upstream side. By this, the gel 200 filling up the hollows or recesses 302 can be drilled together with the crests 303. Therefore, the passage 700 illustrated in FIG. 23A can be enlarged, and a passage 800 larger in diameter than the passage 700 can be obtained.

Thus, according to this embodiment, filling with the gel 200 is conducted such as to form the passage 700 preliminarily, and, therefore, the amount of the gel 200 to be used can be reduced. Consequently, a reduction in cost can be realized.

In the drilling step, the preliminarily formed passage 700 functions as a prepared hole, and, accordingly, the drilling can be reliably carried out straight forward.

While the blood vessel lumen forming method and the medical elongated body according to the present disclosure have been described based on the embodiments illustrated in the drawings, the present disclosure is not limited to these embodiments. The configurations of components and the steps can be replaced by other ones which have the same or equivalent functions to those of the ones described. Also, other structures or steps may be added to the ones according to the present disclosure.

Note that the present disclosure can also be applied, for example, to treatment of aneurysm. In this case, the aneurysm formed by hollowing of a blood vessel wall toward the outside of a blood vessel is filled up with a gel, and thereafter the gel is drilled, whereby a passage in the blood vessel can be sufficiently secured while occluding the aneurysm with the gel.

In addition, while a case in which the blood flow on the upstream side is stopped and the hollows or recesses are filled up with the gel has been described in the filling step in the above embodiments, the present disclosure is not limited to this configuration. For example, in relation to hollows formed in a blood vessel wall, the medical elongated boy may not only be delivered from the downstream side toward the upstream side with respect to the blood flow but also be delivered in the reverse direction, or along the blood flow direction. In either case, a configuration may be adopted in which after the medical elongated body is positioned on the forward or deeper side with respect to the advancing direction of the medical elongated body by way of the hollows or recesses in the blood vessel wall, the gel is jetted into the hollows or recesses while withdrawing the medical elongated body toward the backward side or the operator's side with respect to the advancing direction thereof, to thereby fill up the hollows or recesses with the gel.

While a case wherein thrombus formation has occurred in a rectilinear blood vessel has been described in the above embodiments, the present disclosure is not limited to this configuration. For example, in a case where thrombus formation has occurred in a curved blood vessel, drilling may be conducted following an arcuate path along the curving direction of the blood vessel, whereby the effects of the present disclosure can be produced.

In addition, while a catheter body having a lumen has been illustrated as an example of the elongated body in the above embodiments, the present disclosure is not restricted to this configuration. The elongated body may be composed of a solid body.

The above-disclosed embodiments involve a situation in which the drilling unit is rotated relative to the catheter body, but the present disclosure is not limited to this configuration. A configuration in which the drill is rotated together with the catheter body may also be adopted.

Having described preferred embodiments of the present disclosure with reference to the accompanying drawings, it is to be understood that the present disclosure is not limited to those precise embodiments and that various changes and modifications could be effected therein by one skilled in the art without departing from the spirit and scope of the present disclosure as defined in the appended claims.

What is claimed is:

1. A method for smoothening a rugged blood vessel inner wall surface at a lesion site of the blood vessel so that a through lumen possessing a smoothened inner surface exists in the blood vessel at the lesion site, thereby inhibiting or preventing stagnation or turbulence of blood flow due to the rugged blood vessel inner wall surface at the lesion site, the rugged blood vessel inner wall surface including a plurality of spaced-apart recesses in the blood vessel, the method comprising:
    moving a catheter in the blood vessel to position a distal portion of the catheter adjacent the rugged blood vessel inner wall surface at the lesion site;
    ejecting gel from the distal portion of the catheter while the distal portion of the catheter is positioned adjacent the rugged blood vessel inner wall surface to deliver the gel into the blood vessel;
    filling at least one of the recesses with the gel;
    removing the catheter from the blood vessel after filling the at least one recess with the gel;
    the removing of the catheter from the blood vessel occurring while the at least one recess remains filled with the gel;
    providing the through lumen in the blood vessel so that the through lumen extends from upstream of the gel to downstream of the gel to allow the blood in the blood vessel upstream of the gel to flow past the gel, the forming of the through lumen in the blood vessel including drilling the gel that has filled the at least one recess to remove at least some of the gel filling the at least one recess and form the through lumen in the blood vessel possessing the smoothened inner surface, the through lumen with the smoothened inner surface possessing an inner diameter that varies along a longitudinal extent of the blood vessel;
    detecting both blood pressure on an upstream side of the rugged blood vessel inner wall surface and blood pressure on a downstream side of the rugged blood vessel inner wall surface to identify the side on which the blood pressure is higher; and
    the inner diameter of the lumen with the smoothened surface increasing toward the side on which the blood pressure is higher.

2. The method according to claim 1, further comprising:
    positioning a partition within the blood vessel before ejecting the gel into the blood vessel; and
    stopping blood flow within the blood vessel by the partition.

3. The method according to claim 2, wherein the positioning of the partition within the blood vessel includes positioning the partition to stop blood flow on each of an upstream side of the at least one recess and a downstream side of the at least one recess.

4. The method according to claim 3, wherein the positioning of the partition within the blood vessel includes positioning the partition to stop the blood flow on the upstream side of the at least one recess before stopping the blood flow on the downstream side of the at least one recess.

5. The method according to claim 1, wherein the ejecting of the gel from the distal portion of the catheter includes ejecting the gel from the distal portion toward the rugged blood vessel inner wall surface and while the distal portion of the catheter is positioned at a proximal portion of the rugged blood vessel inner wall surface.

6. The method according to claim 1, further comprising, during the drilling of the gel that has filled the at least one recess, also drilling a part of the rugged blood vessel inner wall surface to remove at least a part of the rugged blood vessel inner wall surface.

7. The method according to claim 1, further comprising:
    imaging the rugged blood vessel inner wall surface to obtain an image of the rugged blood vessel inner wall surface; and the drilling of the gel being performed based on the image obtained during the imaging.

\* \* \* \* \*